United States Patent
Baird et al.

(10) Patent No.: US 6,235,468 B1
(45) Date of Patent: *May 22, 2001

(54) METHOD FOR CHARACTERISING VARIABILITY IN TELOMERE DNA BY PCR

(75) Inventors: Duncan Martin Baird, Dalham; Nicola Jane Royle; Alec John Jeffreys, both of Leicester, all of (GB)

(73) Assignee: Zeneca Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,384

(22) PCT Filed: Oct. 19, 1995

(86) PCT No.: PCT/GB95/02467
  § 371 Date: Apr. 16, 1997
  § 102(e) Date: Apr. 16, 1997

(87) PCT Pub. No.: WO96/12821
  PCT Pub. Date: May 2, 1996

(30) Foreign Application Priority Data
  Oct. 21, 1994 (GB) .................................................. 9421234
  May 25, 1995 (GB) .................................................. 9510639

(51) Int. Cl.[7] .............................. C12Q 1/68; C12P 19/34; C07H 21/04

(52) U.S. Cl. ............................ 435/6; 435/91.2; 435/91.1; 536/24.31; 536/24.33

(58) Field of Search ................................. 435/91.1, 91.2, 435/6, 4; 536/23.1, 24.3, 24.33; 364/496–499; 204/182.8

(56) References Cited

U.S. PATENT DOCUMENTS 5,648,215 * 7/1997 West et al. .............................. 435/6

FOREIGN PATENT DOCUMENTS 530 009 * 3/1993 (EP) .

OTHER PUBLICATIONS

Baird et al: "Mechanisms underlying telomer repeat turnover, revealed by hypervariable variant repeat distribution patterns in the human Xp:Yp telomer.", EMBO Journal, vol. 14, No. 21, Nov. 1, 1995, pp. 5433–5443, see the whole document.*

Brown et al: "Structure and polymorphism of human telomer–associated DNA", Cell, vol. 63, Oct. 5, 1990, pp. 119–132, see the whole document.*

Royle et al: "Isolation of telomer junction fragments by anchored polymerase chain reaction", Proc. Royal Soc. of Lonodn: Biological Sciences, vol. 247, No. 1318, Jan. 22, 1992, pp. 56–67, see p. 62, para 2; Discussion, para 1.*

Baird et al: "Extreme variability in the Xp:Yp pseudoautosomal telomer revealed by telomer variant mapping", American Journal of Human Genetics, vol. 55, No. (3 suppl.), Oct. 18–22, 1994, p. a25, see abstract 123.*

(List continued on next page.)

Primary Examiner—Carla J. Myers
(74) Attorney, Agent, or Firm—Cushman Darby & Cushman

(57) ABSTRACT

A method of characterizing a test sample of genomic DNA which method comprises contacting the test sample with type specific primer to prime selectively, within a telomere repeat array, internal repeat units of that type, and extending the type specific primers in the presence of appropriate nucleoside triphosphates and an agent for polymerization thereof to produce a set of amplification products extending from the internal repeat units of that type to at least the end of the telomere repeat array.

44 Claims, 16 Drawing Sheets-

OTHER PUBLICATIONS

Baird et al. The American Journal of Human Genetics. vol. 55, No. 3, p. A25, abstract 123, Sep. 1994.*

Baird et al: "Mechanisms underlying telomar repeat turnover, revealed by hypervariable variant repeat distribution patterns in the human Xp:Yp telomer.", EMBO JOURNAL, vol. 14, No. 21, Nov. 1, 1995, pp.5433–43, see the whole document.

BROWN et al: "Structure and polymorphism of human telomer–associated DNA", CELL, vol. 63, October 5, 1990, pp.5433–43, see the whole document.

ROYLE et al: "Isolation of telomar junction fragments by anchored polymerase chain reaction", PROC. ROYAL SOC. OF LONODN: BIOLOGICAL SCIENCES, vol. 247, no. 1318, Jan. 22, 1992, pp. 56—7, see pg. 62, para 2; Discussion, para 1.

BAIRD et al: "Extreme variability in the Xp:Yp pseudoautosomal telomer revealed by telomer variant mapping", AMERICAN JOURNAL OF HUMAN GENETICS, vol. 55, No. (3 suppl.), Oct. 18–22, 1994, p.a25, see abstract 123.

* cited by examiner

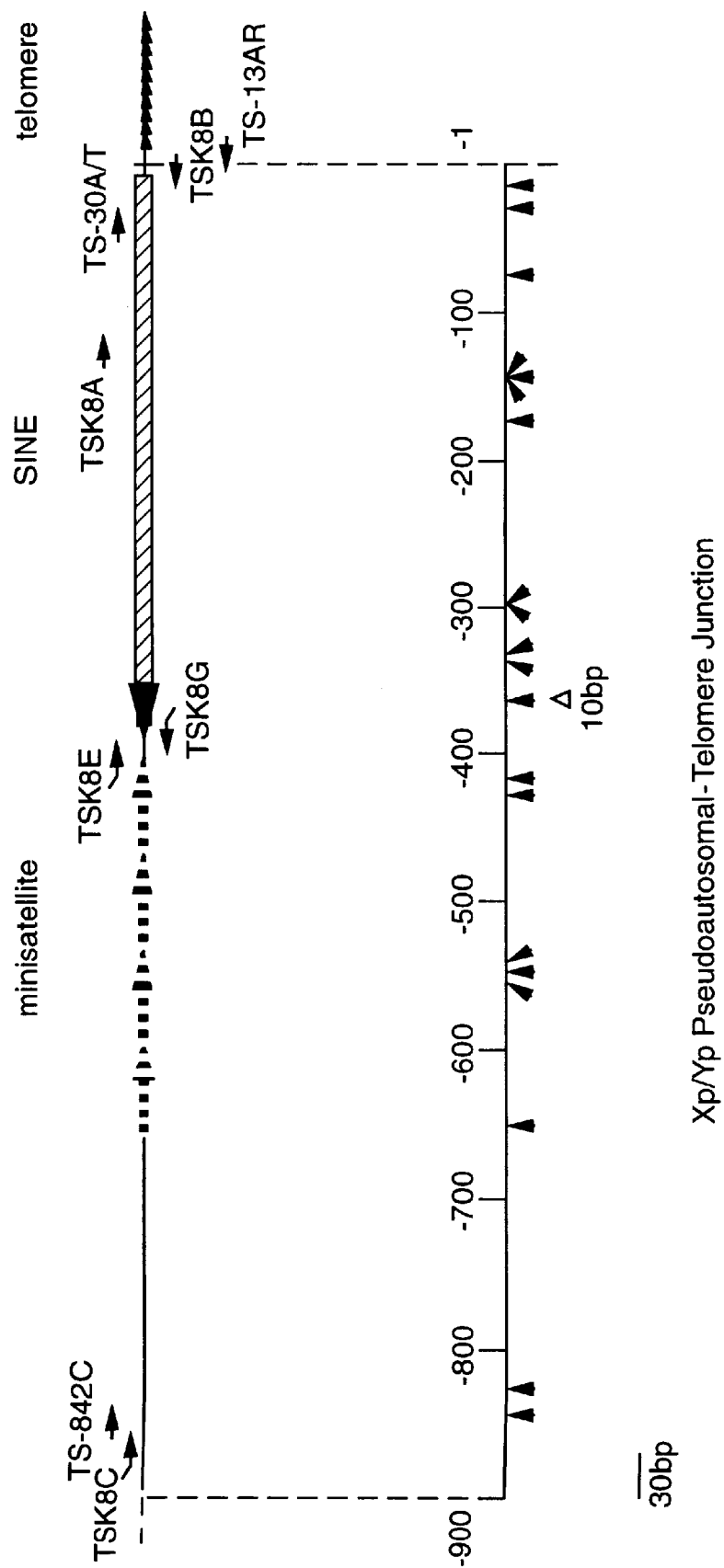
FIG. I(a)

FIG. 1(b)

```
         TSK8C                 TS-842C
      *————→                 ————→
                                              -842 DdeI +/-   -826
-876  cagggaccgg gacaaataga cggggactcc cgagatgaga aagacctttt cgtacaaagt gtttgcatca
                                                           t -806  gtacctcaca atgaaaagaa taagataaat acacagtacaa aaaagcaatc accagatcag ctcaaggcac
                                     c -736  tctttgaagt cccccctgtg tagggaagtt ggaagacata tctgtgtggc ccatagagag tagatcccaa -652 AvaII +/-                                     -554  -544 -540
-666  agacagaagg CCCAAGTCCC CCCCTAAATT CCAGAAGGGA ACTGGGTTAG AGTCCAGGGG CTCATGCAAC GGGCTGTCCC
                 G                                                    A    G  T -596  TGTCCCAGGG CCCCTAAATT CCAGAAGGGA ACTGGGTTAG AGTCCAGGGG CTCATGCAAC GGGCTGTCCC
      TGTACAGGAC CAGGAGCTCA TGTACAGGGC -526  TGGTCCCCTA AATCCCCACA GGGGAACTGG GTTAGAGATG AGGAGCTCAT TTTCCGGGCT GTCCAGGTCC
                                                                        * TSK8E
                                                                        ————→
               -427 TaqI +/-        -415 MboII +/-
-456  CCTAAATCCC AGATGGGAAC TGGGTTATCA ACCAGGTGCT CTTCTAGGGG TTGTctcagg gtcctagtgt
                        G                                       C
                                                                               ←————
                                                                                TSK8G
```

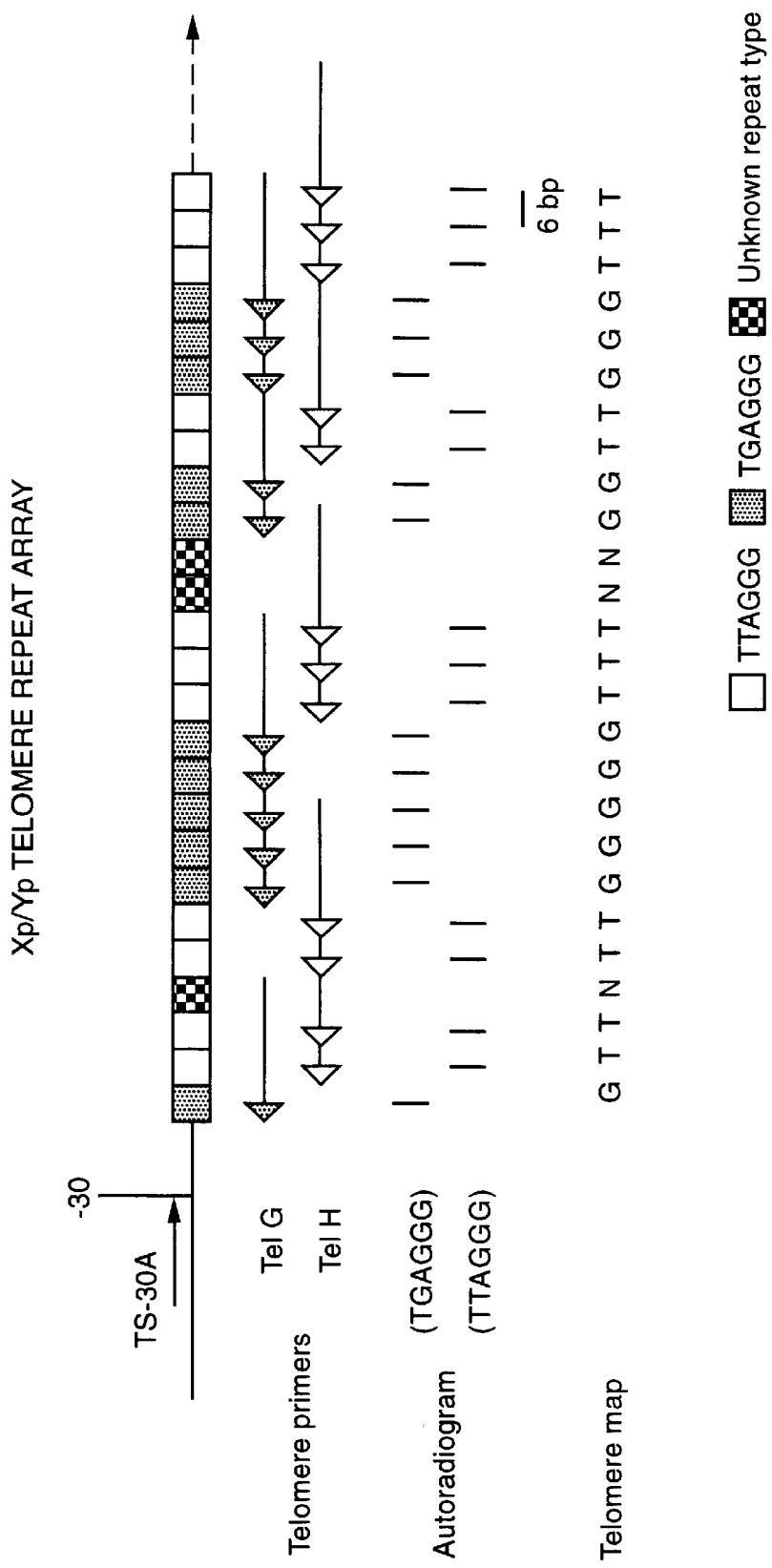

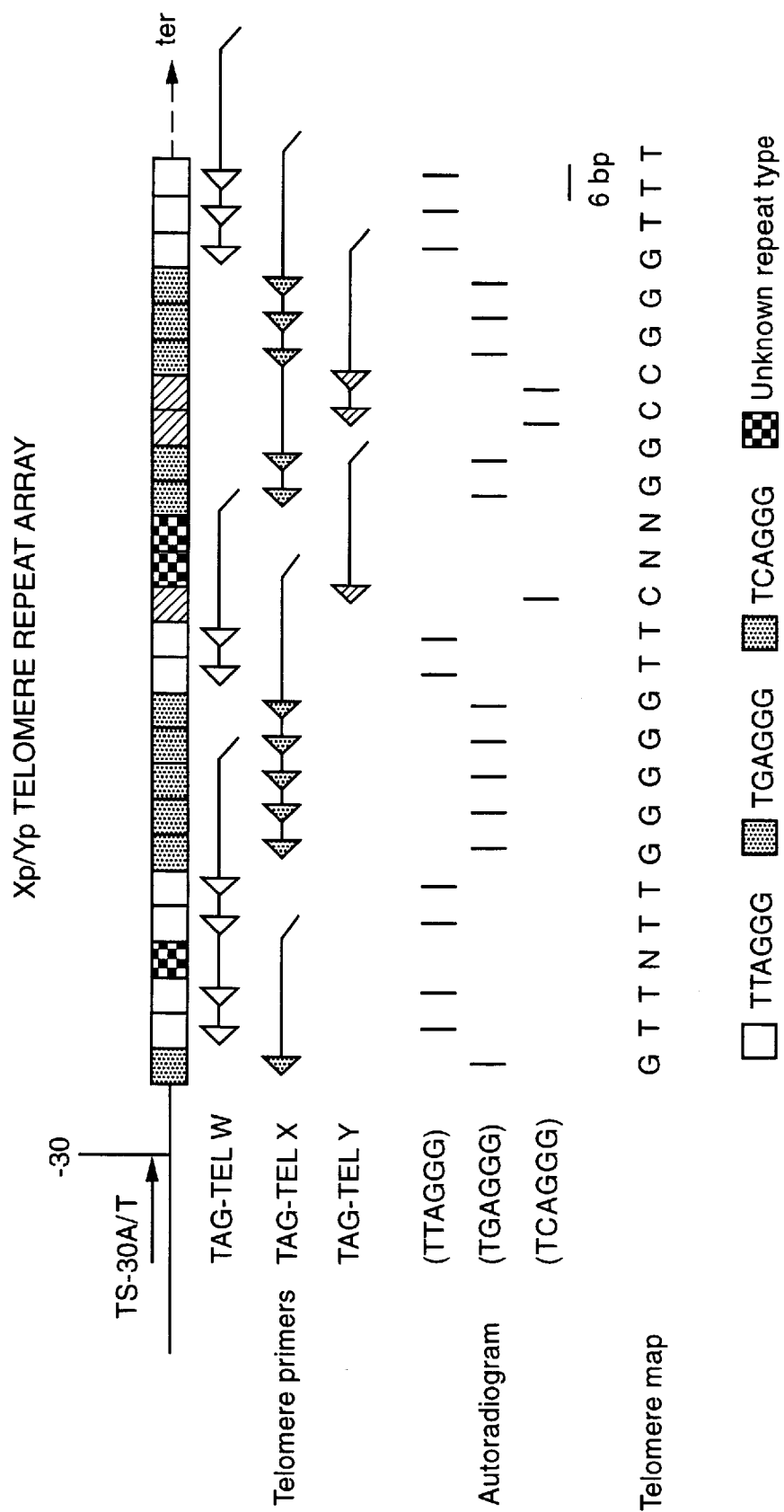

FIG. 6(b)

```
CEPH        Repeat Position
       1         10        20        30        40        50        60
6602   GTTTTNTCNTCNTCCCCCCCCCCCTTNNNNTCTTTTTTTTTTTTTTTTNTTTTT........
1702   GTTTTCTTCNTNTCNNCNNCCCCCCCCCCCTTTTTTTTTGTGGGGGGTTTTGGG........
3502   GTTTTCCCCCCCCCCCCTTTTTTTTTTTTTTTTTTTTTTTTTTTTT........
3701   GTTTTTTTTTTTTTTTTTTTTTTTTTTTTTTTTTTTTTTTTTTTT........
6601   GTTTTTTTTTTNTTTTTTTTTTTTTTTTTTTTTTTTTTTTTTTTT........
```

FIG. 6(c)

FLANKING HAPLOTYPE A

FIG. 6(d)

FLANKING HAPLOTYPE A (CONTINUED)

```
141801  NNGGGGGGG---NNNNNNNNNNNN-NNNNNNNNN----NNNNNNNNNNNNNNNNNNNN---NNNNNN-NN--NN----NN----NNNNN...
  3701
141802  NNGGGGGGG--G----N---------------NNNNNNNNNNNNNNNTNNNNN-NNNNNNNNNNNNNNNNN---NNNN...
141802  NNGGGGGGG--G---NN---------------NNNNNNNNNNNNNNNN--N--NNNNNNNNNNNNNNNNNN---------NNNNN...
134102  NNGGGGGGG--------N--NNN-------N----NN-----N---NN----NNN
  0202
  1702  NNGGGGGGG----------N---N-------N
  6602
141301  NNGGGGGGG--------GG--------GGGGGGGGG--------NNNNNNNNNNNNNNNNNNN
141301  NNGGGGGGG--------G-G--G--G-GG-----------GG-GG--GG-G-----G-GGG-GG-GG-G----GGGG-GG---G---G----GG...
142101  NNGGGGGGG--------G-G--G--G-GG-----------GG-GG--G-G----GGG-G--G------G--G-GGG-GG-G-G--G--GG-GG-G-----
141601  NNGGGGGG---------'------CCCCCCCCCCNNNNNN--N----NNNNN...
        NNG-----------------------------
10202   NNN-CCCNCNCNCNCCNNNNN--C-N-C----CN-CC---NNNNNNNNNNNNNNNNNNNNNNNNNNN-CCCCCCCCCC----GGGGGGGG-GGGGG-G-G-G----GG-GGG-GG-G...
```

FIG. 6(e)

FLANKING HAPLOTYPE B

```
3502        G----CCCCCCCCCCCCCCCCCCCCC----------------------------------------------------------------------------------------...
141302      G---NN-NNCCCCCCCCCCCCCCC-C----------------------------------------------------------------------------------------...
137502      G---NN-NNCCCCCCCCCCCCCCCC-----------------------------------------------------------------------------------------...
133201      G---NN-NN-NN-CCCCCCCCCCCCCCCCNNN-------N-----------------------------------------------------------------------...
141301      G---NN-NN-CCCCNN-NNCNN-CCCCCNN-NNCCCCCCCC-----------N-----------------------------------------------------------...
141802      G---NN-NN-CCCCCCCN--N--NN--CCCCCCCCCCCCCCC--------------------N------------------------------------------------...
142101      G---NN-NN-CCCCCCCCNN-NNCCCCCCCC---------------------------NN--NNN--------NN------------------------------------...
134601      G---NN-NNCCCCCCCC--C---------------------N------N-NN---NN-------N--------------------------------------------...
6602        G---NN-CC-CC-CCCCCCCCC----N-C----N----------------N--NN--NN------------------------------------------------...
1201        G---NN-CN-CCCCCCCCCCC------------------------------N--------------------------------------------------------...
140802      G---CN-NN-N-N-NNCN-CCCCC--CCCCCCCCC-------------N--N-N-N-N-----------------------------------------------...
134102      G---N-CN-CN-CN-CCCCCCCCC----------------------------------------------------------------------------------...
2302        G---N-CN--N-N-CNCCCCCCCCCCCCCCC-CC--CC--C---------------------------------------------------------------...
1702        G-------CN-CN--N-N-CNCNNCCCCCCCCCCCC-----------G-GGGGGGG------GGG-------G-G-GGGGGGGGGG-----GGG...
1329202     G---NN-NN-NNCCCGCCCCCGCGCGGCGGG---G--G--GG--G---G------G---G--G----------------G--G-...
1329401     G---NN-NN-CCCCCCGCGGCGCGCGGCGGCCCCGCGGCGGGNGNCGGCCCCCCCC---------------G-------------------------...
134901      G-------G--GG-GG-GG-G-GG--G-----G------GGG-GGG-----------------------N------------...
88401       G-------N-----------------------------------------N--...
141801      G------------------NNNN-------NNN-------------------------------------------...
6601        G-------N------------------------N--...
```

FIG. 6(f)

FLANKING HAPLOTYPE B (CONTINUED)

```
3701      GN--------------------------------------------------------------------...
10202     GN--------------------------------------------------------------------...
10402     GN--------------------------------------------------------------------...
88402     GN--------------------------------------------------------------------...
133301    GN--------------------------------------------------------------------...
135001    G---------------------------------------------------------------------...
1329102   NN--------------------------------------------------------------------...
```

FLANKING HAPLOTYPE C

```
4501      G---GGNNNNNNNNNNNN--GGGGGGG---GGGGGGG--GG-GG-GG-GG--G-GG-GG-G--------GG-GG-GG--G----G-G-G-G-G-G-G-...
142302    G---GGNNNNNNNNNNNN--GGGGGGG---GGGGGGG--GG-GG-GG-GG--G-GG-GG-G--G----GG-GG-GG----G--G-G-G-G-G--G-G--...
142308    G---GGNNNNNNNNNNNN--GGGGGGG---GGGGGGG--GGGGGGG--GG-GG-GG-G--G--G-G--G--GG-GG--G----G-G-G-G-G--G-GGGGGG...
136216    G---GGNNNNNNNNNNNN--GGGGGGG---GGGGGGG--GG-GG-GG-GG-GG-GG-G--G-G----G-G--GG-GG----G--G-G-G-G--G-GG-G--GGGG.
134003    G---GGNNNNNNNNNNNN--GGGGGGG---GGGGGGG--GG-GG-GG-GG-GG-GG-G---G----G-GG-G--...
141811    G---GGNNNNNNNNNNNN--GGGGGGG---GGGGGGG--GG-GG-GG-G--G-GG-GG-G------G-GG-GG--...
142006    G---GGNNNNNNNNNNNNC-GGGGGGG-GG-G-----N...
1202      G---GGNGNNN-----------...
141601    G---GGNGN---C-CCCCCCCCCCCCCC-------------NN--------...
134114    G--------CCCCCCCCCCCCCCCCCCCCC---------------...
```

METHOD FOR CHARACTERISING VARIABILITY IN TELOMERE DNA BY PCR this application is the national phase of international application PCT/GB95/02467, filed Oct. 19, 1995 which designated the U.S.

The present invention relates to methods of genetic characterisation. In particular it relates to methods based on the analysis of telomeric repeat arrays.

The Xp/Yp pseudoautosomal region (PAR 1) has been well characterized, it is 2.6 mb in length, contains at least 6 genes and it is defined proximally by an Alu-element and telomere at the distal end (Rappold, 1993). In common with the proterminal regions of many human autosomes, the PAR1 has a high GC-content and contains many hypervariable GC-rich minisatellites. During male meiosis chromosome pairing occurs between the homologous regions of the X and Y chromosomes, and the PAR1 is the site of an obligatory recombination event (Cooke et al., 1985, Simmler et al., 1985). Recently a female recombination hotspot has been identified within the PAR1, between the loci DXYS20 (3cosPP) and DXYS78 (pMS600) and only 20–80 kb from the telomere (Henke et al., 1993). Clearly the PAR1 serves a very specialized function in the male germline but it also shares some of the physical and genetic properties that have been attributed to the proterminal regions of human autosomes.

The terminal sequences, including the telomere of the PAR1 have been cloned (Brown, 1989, Royle et al., 1992). DXYS14 (detected by 29C1, Inglehearn and Cooke, 1990) is the most distal hypervariable minisatellite, located within 20 kb of the telomere. Sequences within 1 kb of this telomere contain another PAR1 specific minisatellite which does not show any restriction fragment length variation and a truncated copy of a SINE (Royle et al., 1992). There are an estimated 20,000 copies of this family of SINEs within the genome (La Mantia et al., 1989).

Telomeres protect linear chromosomes from degradation and fusion to other chromosomes, and are thought to be a site of attachment to the nuclear matrix at times during the cell cycle. Telomeres of all human chromosomes are composed of variable length arrays of (TTAGGG) repeat units with the G-rich strand oriented 5' to 3' towards the telomere. Variant telomere repeat units such as (TTGGGG) and TGAGGG) have been identified but tend to be located at the proximal ends of human telomeres (Allshire et al., 1989). Telomeric repeats, in association with telomere binding proteins, are all that is required for a functional telomere and as such they protect the linear chromosome from degradation, fusion to other chromosomes, and they are thought to be a site of attachment to the nuclear matrix at times during the cell cycle (Biessmann and Mason, 1993). Telomere length decreases in somatic tissues with increasing cycles of replication and mitotic cell division (Hastie et al., 1990, Harley et al., 1990) and it is presumed that eventually functional telomeres are lost from chromosomes and the genome is destabilized. The loss of telomere repeats can be counteracted by the activity of telomerase, a specialized reverse transcriptase, which adds (TTAGGG) repeats de novo (Greider and Blackburn, 1989, Morin, 1989) but much evidence suggest that telomerase is only active in the human germline. Recently telomerase activity has been detected in ovarian carcinomas but not in the normal tissue from the patient (Counter et al., 1994) and it has been suggested that reactivation of telomerase is an essential step in tumour progression and in the immortalization of cells in culture (Greider, 1994).

Sequences composed of arrays of tandem repeats range from satellite DNAs to short arrays of dinucleotide repeats found in microsatellites. Analysis of the internal structure of alleles at minisatellite loci has been achieved by mapping the distribution of repeat unites (MVR-PCR, Jeffreys et al., 1991) which show-sequence variation from the consensus repeat. This method has revealed the real extent of allelic variation at several loci (Monckton et al., 1993, Armour et al., 1993, Neil and Jeffreys, 1993, Buard and Vergnaud, 1994) and been used to identify the processes involved in the generation of mutant alleles which arise in the germline (Jeffreys et al., 1994).

Whilst telomere repeat arrays may be expected to show variation, the level of allelic variability between individuals and hence informativeness, identified to date has been limited. We now provide a novel system called telomere variant repeat mapping by PCR (TVR-PCR) which has revealed extensive variation between unrelated alleles.

Therefore in a first aspect of the invention we provide a method of characterising a test sample of genomic DNA which method comprises contacting the test sample with type specific primer to prime selectively, within a telomere repeat array, internal repeat units of that type, and extending the type specific primers in the presence of appropriate nucleoside triphosphates and an agent for polymerisation thereof to produce a set of amplification products extending from the internal repeat units of that type to at least the end of the telomere repeat array.

Two or more specific types of telomere repeat unit may be amplified to generate corresponding sets of amplification products.

The set(s) of amplification products preferably extend to a locus flanking the telomere repeat array and acts as template for a common primer which hybridises to the flanking locus and is extended in the presence of appropriate nucleoside triphosphates and an agent for polymerisation thereof to amplify the set of amplification products. The above amplification procedures may be repeated as required, for example in a polymerase chain reaction.

The test sample of genomic DNA may be total genomic DNA or partially degraded DNA (provided that all or a relevant part of the telomere repeat array to be analysed remains unaffected).

The type specific primer is an oligonucleotide prepared either by synthetic methods or derived from a naturally occurring sequence, which is capable of acting as a point of initiation of synthesis when placed under conditions in which synthesis of a primer extension product which is complementary to a nucleic acid strand is induced, ie. in the presence of appropriate nucleoside triphosphates and an agent for polymerisation in an appropriate buffer and at a suitable temperature. In our European Patent No. 0332435, the contents of which are incorporated herein by reference, we disclose and claim a method for the selective amplification of template sequences which differ by as little as one base as well as type specific primers for use in the selective amplification method. Type specific primers for use in the present invention may therefore be designed with reference to our above mentioned European Patent, Publication No. 0332435. The selective amplification method is now commonly referred to as the Amplification Refractory Mutation System (ARMS). ARMS is a trade mark of Zeneca Limited.

It has been reported elswhere (Jeffreys et al, Nature, 1994, 354, 204–209) that amplification products may shorten progressively at each amplification cycle, due to the type specific primer priming internally on amplification products from previous cycles. Jeffreys et al unexpectedly found that this problem may be overcome by use of a tail specific primer which hybridises to the complement of the tail sequence in the extension product of the common primer and is extended in the presence of appropriate nucleoside triphosphates and an agent for polymerisation thereof to amplify the common primer amplification products. In summary the tail sequence on the type specific primer is selected so that its complement in the extension product of the common primer provides a convenient template for the tail specific primer provided that the tail sequence and complementary sequences do not hybridise to the tandemly repeated region or to an adjacent region. Examples of convenient tail sequence lengths include up to 50, up to 40, up to 30 and up to 20 nucleotides. Further details regarding the use of tailed primers are disclosed in UK patent application, publication no. 2259138 incorporated herein by reference.

Remarkably we have found that in TVR-PCR it is not essential to 'tag' primers with a non-complementary tail as above.

The sets of amplification products prepared according to the above procedures are conveniently amplified in a polymerase chain reaction. The polymerase chain reaction is conveniently described in "PCR Technology" edited by Henry A. Ehrlich, published by Stockton Press—London/New York in 1989. If required, a tail sequence on the type specific primer ensures that the tail specific primer primes internal repeat units of the desired type at each amplification cycle.

The set of amplification products is separated to provide a sample code according to any convenient procedure provided that the separation is carried out on the basis of the native (genomic) order of the individual telomeric repeat units of a specific type within the telomere repeat array. It will be appreciated that the sample code may be provided from any convenient number of amplification products within the set and representing any convenient number of positions within the native order. In general, separation is effected on the basis of the relative sizes of the amplification products and these are conveniently separated via known gel electrophoresis techniques resulting in a ladder of amplification products representing the sample code. Direct visualisation of the amplification products, for example using staining procedures, and in particular ethidium bromide, are preferred. If required however the amplification products may be identified using a probe which for example hybridises specifically to the tandemly repeated region or to a flanking region. The probe may comprise any convenient radioactive label or marker component. Preferably a non-radioactive label such as the triggerable chemiluminescent 1,2-dioxetane compound Lumi-Phos$^{530}$ disclosed and claimed in U.S. Pat. No. 4,959,182 is employed. Lumi-Phos$^{530}$ is a trade mark of Lumigen Inc.

As indicated earlier above the method of the present invention may be used to analyse at least two specific types of telomere repeat unit within the telomere repeat array. This increases considerably the informativeness of the resulting sample code. Where amplification is effected using type specific primers this also provides integral control of any mispriming on non-type specific internal repeat units. Thus for example the amplification products are separated as above to provide two or more type specific ladders of amplification products.

In general the method of the present invention is carried out with reference to one or more controls. In particular the method is carried out with reference to a control sample of known profile. Thus for example where the amplification products are provided as type specific ladders the positions of the individual "rungs" are compared with the ladder profile for the control sample. The ladder profile for the control sample may also conveniently provide reference positions throughout the telomere repeat array for internal repeat units of a specific type comprised in the sample code.

Ideally the internal telomere repeat units of a specific type and included in the sample code are of invariant length. This simplifies analysis of, for example type specific ladder (s) of amplification products.

The flanking locus is advantageously polymorphic since the test sample may be further characterised with respect to any informative sequence polymorphism at this locus. By "informative sequence polymorphism" we mean any sequence polymorphism which provides a useful degree of information within a population to be analysed. Convenient polymorphisms are in general detected in about 1%–50% of a given population, such as in up to 2%, up to 5% or up to 10% of individuals.

Amplification of a selected sequence variant of the common locus is conveniently effected using a type specific ie. allele specific common primer in a manner directly analogous to the repeat unit type specific primers of the present invention. Thus, the allele specific common primer is extended in the presence of appropriate nucleoside triphosphates and an agent for polymerisation thereof to amplify a set of amplification products comprising the selected sequence variant. The allele specific common primers are conveniently designed and produced as described earlier above with reference to the type specific primers and our European patent, publication no. 0332435.

The above aspect of the invention may advantageously be used to characterise the test sample of genomic DNA in respect of either or both maternal and paternal alleles without prior separation of the alleles. By way of example, sample DNA from an individual who is heterozygous for a selected variant of the common locus will only give rise to type specific common primer amplification products from one allele. Similarly, sample DNA from an individual who does not possess the selected variant will not give rise to any common primer amplification products. Any such results may be conveniently verified by using a non-type specific common primer at the same common locus to provide amplification products for both alleies. In general, for routine characterisation purposes a non-type specific common primer will be employed to obtain information from both alleles.

We have studied sequences adjacent to the PAR1 telomere and identified a high frequency of base substitution polymorphisms and one insertion/deletion polymorphism. Seven of the polymorphic positions were studied extensively and they show almost complete linkage disequilibrium with one another defining only three haplotypes. The haplotypes vary in frequency between different ethnic poppulations. In order to study allelic variation present within the PAR1 telomere itself we developed the TVR-PCR system disclosed above.

Designing flanking primers for use with the PAR1 telomere repeat array was not straightforward. Many unique sequence primers failed to amplify the telomere repeat array in an informative manner. We have surprisingly found that a short interspersed repetitive element (SINE) flanking the PARI telomere comprises a polymorphic site suitable for allele specific amplification. This is unexpected not least since this family of SINES has at least 20,000 copies in the genome which does not bode well for allele specific amplification.

Within one kilobase of the Xp/Yp pseudoautosomal region (PAR1) telomere repeat array we have identified polymorphic loci (cf. FIG. 1A).

In a further aspect of the invention we provide a method of characterising a test sample of genomic DNA which comprises contacting the test sample with allele specific primers to prime selectively at one or more polymorphic loci within one kilobase of the Xp/Yp pseudoautosomal region (PAR1) telomere repeat array in the presence of appropriate nucleoside triphosphates and an agent for polymerisation and detecting allelic variants by reference to the presence or absence of primer extension product(s).

The primer extension product of one allele specific primer can act as the template for an allele specific primer for a different polymorphic locus in a polymerase chain reaction.

In particular we disclose the analysis of one or more polymorphisms selected from positions −13, −30, −176, −414, −427, −652, −842 as determined from the end of the Xp/Yp pseudoautosomal region (PAR1) telomere repeat array. Also in particular the common primer is an allele specific primer for one of the, −13, −30, and −176 polymorphisms.

The size of the amplification products is governed primarily by practical considerations. On conventional polyacrylamide gels enables products of up to about 1 kilobase, conveniently of up to 600 bases, may be resolved satisfactorily.

A significant advantage of our claimed method is that the genomic DNA sample to be tested does not require any elaborate pre-treatment. If desired appropriate pre-digestion may be employed. Thus the DNA sample may comprise total genomic DNA, including mitochondrial DNA.

By "genomic DNA" we mean nucleic acid, such as DNA, from any convenient animal or plant species, such as humans, cattle, and horses, especially humans. Known DNA typing procedures have already been effected on a wide variety of species.

In a further aspect of the method of the present invention two or more sets of differentially labelled amplification products are prepared simultaneously. Convenient labels include specific binding substances such as biotin/avidin and also immunogenic specific binding substances. Further convenient labels include chromophores and/or fluorophores such as fluorescein and/or rhodamine. In general the relevant primers are labelled although other methods of providing labelled amplification products are not excluded.

In any relevant preceding aspect of the present invention different type specific and/or allele specific primers may comprise different tail sequences to facilitate separation of the amplification products.

A significant advantage of the method of the present invention is that it provides a sample code individual to the genomic DNA sample. Depending on the procedure used to separate the set(s) of amplification products the sample code may already be in machine readable form, for example suitable for scanning and digital encoding.

Therefore according to a further aspect of the present invention we provide an individual sample code prepared according to any preceding aspect of the present invention. The sample code-may be based on any convenient number of coding states such as at least 2, for example at least 3, at least 4, at least 5, at least 6, at least 7, at least 8 or at least 9 coding states. All the above are independent and convenient numbers of coding states.

We also provide a database which comprises a multiplicity of individual sample codes prepared as above.

The above database may be established and used for any convenient characterisation purposes, such as in the identification of individuals and the determination of individual relationships.

We also provide a primer for use in the method of the invention which hybridises to a locus specifically identifiable by one of:

```
TSK8A   (SEQ ID NO:1) 5'-GAGTGAAAGAACGAAGCTTCC-3'
TSK8B   (SEQ ID NO:2) 5'-CCCTCTGAAAGTGGACCTAT-3'
TSK8C   (SEQ ID NO:3) 5'-GCGGTACCAGGGACCGGGACAAATAGAC-3'
TSK8E   (SEQ ID NO:4) 5'-GCGGTACCTAGGGGTTGTCTCAGGGTCC-3'
TSK8G   (SEQ ID NO:5) 5'-CGGAATTCCAGACACACTAGGACCCTGA-3'
TSK8J   (SEQ ID NO:6) 5'-GAATTCCTGGGGACTGCGGATG-3'
TSK8K   (SEQ ID NO:7) 5'-CATCCCTGAAGAAGCATCTTGGCC-3'
```

We also provide a primer for use in the method of the invention which hybridises to a locus specifically identifiable by one of:

```
TS-842C  (SEQ ID NO:8)  5'-AGACGGGGACTCCCGAGC-3'
TS-30A   (SEQ ID NO:9)  5'-CTGCTTTTATTCTCTAATCTGCTCCCA-3'
TS-30TS  (SEQ ID NO:10) 5'-CTTTTATTCTCTAATCTGCTCCCT-3'
TS-13AR  (SEQ ID NO:11) 5'-ACCCTCTGAAAGTGGACCA-3'
TS-30T   (SEQ ID NO:22) 5'-CTGCTTTTATTCTCTAATCTGCTCCCT-3'
```

We also provide a primer for use in the method of the invention which hybridises to a locus specifically identifiable by one of:

TelH (SEQ ID NO:12) 5'-CCCTAACCCTAACCCTAACCCTA-3'

TelG (SEQ ID NO:13) 5'-CCCTCACCCTCACCCTCACCCTC-3'

TelW (SEQ ID NO:14) 5'-CCCTTACCCTTACCCTNACCCTA-3'

TelX (SEQ ID NO:15) 5'-CCCTTACCCTTACCCTNACCCTC-3'

TelY (SEQ ID NO:16) 5'-CCCTTACCCTTACCCTNACCCTG-3'

We also provide a test kit which comprises one or more type specific primer(s), and/or allele specific and/or common primer(s) for use in the method of the invention. The test kit may comprise at least two complementary type specific primer(s) as defined above together with optional common primer as defined above and/or optional tail specific primer as defined above, the test kit further including appropriate buffer, packaging and instructions for use. The test kit conveniently further comprises appropriate nucleoside triphosphates and/or an agent for polymerisation thereof. Additional optional items for inclusion in the test kit include control DNA of known profile, an optionally labelled probe for the telomeric repeat array and a probe detection system.

The invention also relates to a computer when programmed to record individual sample codes as defined above. Further independent aspects of the present invention relate to a computer when programmed to search for similarities between individual sample codes as defined above and to a computer when programmed to interrogate a database as defined above.

We also disclose the use of the method of the invention for the detection in a test sample from an individual of inherited or acquired disease, or for the detection of a predisposition to inherited or acquired disease. In particular the method of the invention may be used in the diagnosis of abnormal cell division and/or growth including cancer.

The term "tandem repeat" is used herein to refer to at least 2 repeats of a sequence comprising at least one sequence polymorphism in a given population. In general the tandemly repeated region used in the method of the present invention comprises at least 5, or at least 10, or at least 15 tandem repeats, such as at least 20 or at least 30, 40, 50 or at least 100 tandem repeats.

The term "set of amplification products" is used herein to refer to a plurality of amplification products which identify the relative positions of internal repeat units of a specific type within the tandemly repeated region. Any convenient number of amplification products are comprised in the set such as at least 2, at least 5, at least 10, at least 15, at least 20, or at least 30 amplification products.

The term "more than one type of repeat unit" is used herein to refer to types of internal repeat units within the tandemly repeated region which may be distinguished according to an informative sequence variation. By way of example the presence or absence of a particular restriction site in a repeat unit provides two types of repeat unit ie. a first type of repeat unit which comprises the particular restriction site and a second type which which does not comprise the particular restriction site. Accordingly the first and second types of repeat unit are "internal repeat units of a specific type". It will be understood that a further informative sequence variation between internal repeat units provides further types of repeat unit and allows further and independent characterisation of the tandemly repeated region.

The term "informative sequence variation" is used herein to indicate sequence variation which provides a useful degree of information within a population to be analysed.

The term "nucleoside triphosphate" is used herein to refer to nucleosides present in either DNA or RNA and thus includes nucleosides which incorporate adenine, cytosine, guanine, thymine and uracil as base, the sugar moiety being deoxyribose or ribose. In general deoxyribonucleosides will be employed in combination with a DNA polymerase. It will be appreciated however that other modified bases capable of base pairing with one of the conventional bases adenine, cytosine, guanine, thymine and uracil may be employed. Such modified bases include for example 8-azaguanine and hypoxanthine.

The term "nucleotide" as used herein can refer to nucleotides present in either DNA or RNA and thus includes nucleotides which incorporate adenine, cytosine, guanine, thymine and uracil as base, the sugar moiety being deoxyribose or ribose. It will be appreciated however that other modified bases capable of base pairing with one of the conventional bases, adenine, cytosine, guanine, thymine and uracil, may be used in the diagnostic primer and amplification primer employed in the present Invention. Such modified bases include for example 8-azaguanine and hypoxanthine.

In addition, it will be understood that references to nucleotide(s), oligonucleotide(s) and the like include analogous species wherein the sugar-phosphate backbone is modified and/or replaced, provided that its hybridisation properties are not destroyed. By way of example the backbone may be replaced by an equivalent synthetic peptide.

By "substantially complementary" we mean that a primer sequence need not reflect the exact sequence of the template provided that under hybridising conditions the primers are capable of fulfilling their stated purpose. In general, mismatched bases are introduced into the primer sequence to provide altered hybridisation stringencies. Commonly, however, the primers have exact complementarity except in so far as non-complementary nucleotides may be present at a predetermined primer terminus as hereinbefore described.

The invention will now be illustrated but not limited by reference to the following specific description, Example, Tables and Figures.

Identification of Polymorphisms in the DNA Adjacent to the Xp/Yp Telomere

Single stranded conformational polymorphism (SSCP) analysis (Orita et al., 1989, P.N.A.S., 86, 2766–2770) on the 480 bp proximal to the start of the Xp:Yp telomere reveals a high level of variation (data not shown). To determine the nature of this variation, direct sequence analysis of PCR products (TSK8C to TSK8G and TSK8E to TSK8B, FIG. 1a) covering 850 bp of DNA flanking the telomere has been undertaken and sequence information was obtained from 32 Caucasian and 21 African DNAs. The sequence is numbered from the first base (−1) flanking the start of the telomere repeat array (defined by a variant GAGGG repeat). The polymorphic positions are distributed throughout the 850 base sequence (FIG. 1, Table 1). Thirteen polymorphisms were identified in Caucasian and 16 in African DNAs, in addition to a 10 bp insertion/deletion polymorphism which was only found among African DNAs (Table 1). The frequency of base substitutional polymorphisms is 1 per 65 bp in Caucasians and 1 per 50 bp in Africans over the 850 bp adjacent to the Xp/Yp telomere. In addition, some rare variant positions were detected but occured only once among the sequenced DNAs and these have not been included in the analysis of this region.

Assaying the Polymorphic Positions

Some of the polymorphisims, create or destroy restriction enzyme sites and initially four of these sites, −414, −427, −652, −842 were selected for further analysis by PCR amplification of genomic DNA using primers TSK8C+TSK8G (FIG. 1a) followed by digestion with one of the appropriate enzymes (MboII, TaqI, AvaII, DdeI, respectively). Each of these polymorphic sites was found to be in Hardy-Weinberg equilibrium in the Caucasian (n=80), African (n=28) populations tested (data not shown). Surprisingly a number of individuals homozygous at all four polymorphic positions were identified among the unrelated Caucasians tested and others were heterozygous at all four positions. Therefore haplotype analysis was carried out by PCR amplification with an ARMS PCR primer for the specific amplification of one of the two alleles (Newton et al., 1989, N.A.R. 17, 2503–2516) at the polymorphic position −842 (primers TS-842C+TSK8G) followed by RFLP analysis to assay the −414, −427 and −652 positions. Haplotype analysis of the 4 polymorphic positions in Caucasians revealed only three (A, B, and C) of the possible 16 haplotypes. Haplotypes A, B and C have frequencies of 0.51, 0.44 and 0.05 respectively in Caucasians and they are in Hardy-Weinberg equilibrium (Table 2). Haplotypes B and C differ only at position −427 and therefore there is almost complete linkage disequilibrium between the 4 polymorphic sites.

RFLP and haplotype analysis of DNAs from Japanese, African, Afro-Caribbean and Karitiana populations was also carried out for the four polymorphic sites. The same three haplotypes were identified in the Japanese, African and Afro-Caribbean populations and although the haplotype frequencies vary, all the tested populations are in Hardy-Weinberg equilibrium (Table 2). The Karitiana are an inbred tribe from South America and only haplotype B was identified among the 22 individuals analysed. Therefore it seems likely that haplotype B is fixed in the Karitiana tribe.

An RFLP assay was established for the −176 polymorphic position based on the precence or absence of a DdeI restriction site. Among the 79 Caucasians DNAs tested, all DNAs heterozygous for the haplotypes (A, B and C) were also heterozygous at the −176 polymorphism and DNAs homozygous for the A or B haplotypes were homozygous at −176, with either a G or T respectively (Table 1).

An ARMS PCR assay for the −30 position was developed (see materials and methods) and analysis showed that among Caucasians, chromosomes with a B or C haplotype had an A at this position, and the majority of chromosomes with a haplotype A had a T at this position with only one haplotype A chromosome having an A −30 (see Table 1). During the analysis of the −176 and −30 polymorphisms a previously undetected polymorphism was identified which reduced the efficiency of amplification with the TSK8B primer. Sequence analysis (see materials and methods) showed that this was due to a polymorphism at the −13 position 3 bp from the 3′ end of the TSK8B primer. An ARMS assay was developed for this position (see materials and methods) and again among 79 Caucasians DNAs assayed, all DNAs homozygous for haplotype A had a T at this position, all DNAs for the B or C haplotypes had an A and all heterozgotes were heterozygous (T/A) at the −13 position. Therefore in Caucasians there is almost complete linkage disequilibrium across the polymorphic positions assayed in Caucasians.

Determining the Sequence Divergence Between the Haplotypes

Unexpectedly nearly complete linkage disequilibrium has been identified between the 7 polymorphic sites (−13, −30, −176, −414, −427, −652 and −842) adjacent to the Xp/Yp telomere in Caucasians DNAs and similarly nearly complete linkage disequilibrium has been demonstrated across 4 polymorphic sites in Africans, Japanese and Afro-Caribbeans (−176, −13, and −30 not tested). In order to determine whether the intervening polymorphic sites were also in strong linkage disequilibrium 3 Caucasian DNAs homozygous for haplotype A and 3 homozygous for B were sequenced (FIG. 2). Every individual sequenced was homozygous for the intervening polymorphic positions and therefore these sites may also be in complete linkage disequilibrium with the Caucasian haplotypes (A or B). The 13 polymorphisms identified in the 850 bp from Caucasian DNAs sequenced (Table 1) represents a 1.6% sequence divergence between the A and B haplotypes.

African DNAs homozygous for haplotypes A and C, the most common haplotypes in this population, were also sequenced. Among the 6 DNAs sequenced the majority of intervening polymorphic positions were homozygous, with the exception of two DNAs (see below and Table 1). In African DNAs there are 14 base substitutional polymorphisms (not including the −13 or −30 positions) and one 10 bp insertion/deletion in the 820 bp sequenced which represent a polymorphic position every 57 bp and up to 1.8% sequence divergence between African haplotypes A and C. One of the sequenced African DNAs was homozygous for haplotype C, but heterozygous at two intervening positions (−544 and −540), and another African DNA homozygous for haplotype A, was also heterozygous at the −544 and −540 polymorphic positions. Further sequence analysis (not included in Table 1) has identified another African DNA homozygous for haplotype A, and homozygous at all the intervening polymorphic positions but with G and T at the −544 and −540 positions respectively. The apparent switch between the African A and C haplotypes across the −544 and −540 positions could have arisen as an interallelic conversation or an intra-allelic exchange between two of the minisatellite repeat units. The additional haplotypes identified after sequencing the intervening polymorphic positions of African DNAs suggests that there is increased heterogeneity within this population, although there is still strong linkage disequilibrium across the polymorphic sites.

Sequence comparison of 3 Caucasian and 3 African DNAs homozygous for haplotype A (based on the −414, −427, −652 and −842 positions) has shown some significant differences at the intervening polymorphic positions (Table 1). When the intervening polymorphic positions are included the A haplotypes are not identical between the African and Caucasian populations but differ at 8 of 18 sites. In addition two other polymorphisms have been detected by sequence analysis; one at position −826 (C→T) occurs only in a subject of African chromosomes with an A haplotype and the other at position −217 (G→C) occurs only on a subset of Caucasian A haplotype chromosomes. These additional variants at −826 and −217 may have arisen recently and be limited to African and Caucasian populations respectively.

Defining the Proximal Limit of the High Frequency of Base Substitional Polymorphisms Sequence information from clone T7A1/4 (Brown et al., Cell (Cambridge, Mass.), 63, 119–132) which includes 2 kbp of DNA adjacent to the Xp/Yp telomere was used to design primers 2.0 and 1.5 kbp from the telomere. Direct sequence analysis of 320 bp from TSK8J to TSK8K PCR products of 17 Caucasian and 11 African DNAs revealed one additional polymorphic position (−1888, G or A) common to both populations and another polymorphic position (−1897, G or A) only in the African DNAs. The frequency of base substantial polymorphisms in this region is reduced compared to the 850 bp adjacent to the telomere in Caucasians and Africans but the difference is not significant (for Caucasians p=0.224 and for Africans p=0.176 using a two tailed probability test). The −1888 polymorphism can be detected by the presence or absence of an NlalV restriction site and was found to be in Hardy-Weinberg equilibrium in Caucasian, Japanese, African and Afro-Caribbean populations (Table 3(a)). Haplotype analysis between the −1888 polymorphism abd flanking haplotypes A, B and C was investigated in Caucasians (Table 3(b)) and strong but incomplete linkage disequilibrium between the flanking haplotypes and the −1888 allele and flanking haplotype frequencies in Africans and Afro-Caribbeans (Table 2(b)) suggests that there is much weaker linkage disequilibrium between the flanking haplotype and −1888 polymorphism in these populating. It seems likely that the very high frequency of base substitutional polymorphisms combined with near complete linkage disequilibrium is confined to the extreme end of the PAR1 adjacent to the telomere.

Telomere Variant Repeat Mapping by PCR (TVR-PCR)

We have developed a system to assay the distribution of variant repeats in the proximal 1 kb of the Xp/Yp telomere. Briefly the method includes amplification of genomic DNA using a radioactively labelled flanking primer which anneals to DNA adjacent to the telomere repeat array with either a (TTAGGG) repeat primer (TELH) or a (TGAGGG) variant repeat primer (TELG). The end-labelled amplified products are resloved on denaturing poly-acrylamide gels and detected by autoradiography. Ladders of bands based on a 6 bp repeat unit are produced and the interspersion pattern of the (TTAGGG) repeats with (TGAGGG) and non amplifying 'null' repeats can be seen (FIG. 3(a)).

Initially amplification into the Xp/Yp telomere was carried out with primer TSK8E which anneals to unique sequence DNA within the genome. However the amplified products included approximately 400 bp of telomere flanking DNA and were not of suitable size for the resolution on polyacrylamide gels. Consequently amplification from the −30 polymorphic position, within the SINE adjacent to the Xp/Yp telomere using primer TS-30A, is carried out. In individuals heterozygous for the flanking haplotypes (AB or AC), the TS-30A primer specifically amplifies from the B or C haplotype into the telomere. The TELG (TGAGGG) and TELH (TTAGGG) repeat primers are composed of 4 repeats and anneals to the G-rich strand of the telomere. The 3' base of these primers mismatches the second position of a 6 bp repeat unit (TT/GAGGG), see Table 4. Under optimised PCR conditions TELG and TELH only initiate amplification when the base in the second position of a repeat unit within the telomere array is complementary to the primer. FIG. 4 shows allele specific amplification of telomeres from unrelated individuals heterozygous at the −30 flanking polymorphic posicion. The first repeat unit of each ladder is (GAGGG) and it is amplified inefficiently by the TELG primer. By resolving the samples on a standard 6% and extension 5% poly-acrylamide gradient gels it is possible to resolve 100 repeat units into the telomere repeat array.

TVR-PCR analysis has been carried out on DNA from the parents of the CEPH panel who are heterozygote for the −30 flanking polymorphism. Among 41 Xp:Yp telomeres mapped to date, 5 are identical because they are composed entirely of telomere (TTAGGG) repeat types at the proximal end of the Xp/Yp telomere. The remaining 36 telomeres are all different, although a subset of maps show similarities and having haplotype C in the flanking DNA suggesting a commom ancestry (data not shown). The Karitiana DNAs are all homozygous for the flanking haplotype B (Table 2), therefore TVR-PCR analysis of the Xp/Yp telomere from the −30 position in these individuals generates a diploid code which cannot easily be interpreted into telomere codes. However, examination of the patterns generated indicate that 10 of the 14 diploid codes examined were different, consequently there must also be variation in the telomere maps of this inbred tribe (data not shown).

Currently Mendelian segregation of telomere maps can be observed within families when at least one parent is heterozygous for A or T at the −30 position. The allele-specific primer, TS-30A, gives rise to a telomere map from any chromosome which has an A at the −30 position. Therefore, a haploid telomere map is generated from individuals who are homozygous for A or T at this position, respectively. Consequently segregation of telomere maps from chromosomes carrying an A at the −30 position can be followed in families when one parent is heterozygous (FIG. 5a). The origin of these muation events (germline, somatic or in cell culture) has not yet been determined.

Refinements of the TVR-PCR Technique

Large gaps at the proximal ends of some of the telomere maps (FIG. 4a) reflect the presence of additional variant repeat types, and from sequence analysis of cloned telomeres (Royle et al., Proc. Roy.Soc.Lond.B., 247, 57–61. 1992) we know that (TCAGGG) and (TTGGGG) repeats are common. When tandem arrays of null repeat types are present in the telomere maps it can be difficult to generate a code of the telomere map for database analysis. Therefore additional telomere and variant repeat primers (Table 4) have been synthesized. The primers TELW, TELX and TELY are all composed of four repeat units; as before the 3' base mismatches on the second position of a 6 bp repeat unit such that TELW, TELX and TELY anneal to (TTAGGG), (TGAGGG) and (TCAGGG) repeat types respectively; a redundancy has been introduced into the second position of the second repeat; and the second position of the two 5' repeats is a T, as our investigations suggest that few (TAAGGG) repeat types occur in telomere repeat arrays. Preliminary experiments with these primers show that "3 state" TVR maps can be produced (FIG. 6). The frequency of null repeats is reduced and amplification of repeat units which occur singly within the telomere repeat array rather than as a block of identical repeats is much improved. As a result it is now possible to code telomere maps and generate a database.

Allele specific amplification from haplotype A alleles with a TS-3OT primer is inefficient, therefore modifications to the primer design have been made. The TVR primers TAG-TELW, TAG-TELX and TAG-TELY are all composed of four repeat units; the 3' base mismatches the second position of a 6 bp repeat unit such that TAG-TELW, TAG-TELX and TAG-TELY anneal to TTAGGG, TGAGGG and TCAGGG repeat types respectively. The corresponding position in the penultimate repeat was made ambiguous to aid equal amplification from different repeat types. Our investigations have indicated that few TAAGGG repeat types occur in human telomere repeat arrays. Therefore the presence of two repeats complementary to TAAGGG at the 5' end of the TAG-TEL primers allow the primers to anneal with reduced efficiency to TTAGGG, TGAGGG, or TCAGGG repeats. In addition, a 20 nucleotide non-complementary tail has been added to the 5' end of each TVR primer but the TVR-PCR reactions do not include addition of a tail-primer to drive the amplification and prevent collapse of the tandemly repeated products. However, the presence of a non-complementary tail was found to promote equal amplification of products from each repeat unit within the telomere repeat array and reduced the generation of additional bands at the end of a block of uniform repeat types.

Allele-specific amplification of telomeres from unrelated individuals heterozygous at the −30 flanking polymorphic position can be performed. TVR-PCR products are resolved as a 6 bp ladder with a band appearing in one of the three tracks (T, G, or C) for each repeat position. Some repeats fail to amplify, presumably due to the presence of additional telomere repeat sequence variation; such unknown repeats have been termed N-type repeats. About 120 repeat units can be resolved on denaturing polyacrylamide gels and the pattern of bands can be readily converted to telomere codes of T-, G-, C- and N-type repeats for database analysis (FIGS. 3 and 4.

Mendellan Inheritance of Xp/Yp Telomeres

The Mendelian inheritance of Xp/Yp telomere maps has been verified in families and the segregation of the paternal telomere maps in CEPH family 1423 is shown in FIG. 5. In this family, the grandfather (1423-11) was heterozygous (A/T) at the −30 position and a telomere map (designated A') was generated by amplification with the allele specific primer, TS-30A. The grandfather (1423-12) was homozygous (A/A) at the −30 position and generated a diploid pattern from the two telomere maps, A and A" telomere contributed only a few bands to the diploid map, probably because many N-type repeats were present at the proximal end of this telomere. The father (1423-01) was also homozygous at the −30 position and inherited the paternal A' and maternal A telomere maps, which produced a diploid pattern different from that seen in his mother. The haploid telomere map amplified in the son (1423-03) was identical to the A' telomere map in the grandfather, while the haploid telomere map (A) in the daughter can be seen as part of the diploid telomere pattern in her father and grandmother. The telomere maps therefore segregate as Mendelian markers both in this family and in six other CEPH families (data not shown). The extreme variability at the proximal end of the PAR1 telomere must be maintained by a relatively high de novo mutation rate, but no mutant alleles have been identified to date among the seven families examined.

Telomere Variability

Telomere maps were established for 65 alleles from the parents of the CEPH family DNAs heterozygous for the −30 flanking polymorphism (FIG. 6c). One of the telomere maps associated with flanking haplotype A and nine associated with haplotype B were composed almost entirely of TTAGGG repeats. Five of the haplotype B alleles were indistinguishable but all other telomeres were different, giving 61 different allelic structures in 65 telomeres mapped. All haplotype A alleles began with at least two N-type repeats, therefore including 12 bp of unknown sequence. Whereas all telomeres associated with flanking haplotype B and C began with a G-type repeat, with the exception of haplotype B telomere 1329102 which like most of the A haplotype telomeres began with two N-type repeats. The variant repeats within the telomeres showed a strong tendency to cluster, to produce for example runs of G- and N-type repeats in haplotype A alleles and C-type repeats in haplotype B alleles. In some cases there was evidence of a higher order repeat structure, for example runs of a TGG three repeat motif in some haplotype C alleles (as seen in 4501). TVR-PCR with an additional TVR-primer has shown that many N-type repeats in haplotype A alleles were TTGGGG (data not shown). occasionally a change in the 6 bp periodicity of the ladder of bands was detected, for example in haplotype A 1201 and related telomeres (FIG. 6) and sequence analysis has shown that additional as yet uncharacterised variants exist amongst other N-type repeats. Clearly the underlying sequence variation at the proximal ends of the Xp/Yp telomeres is greater than is currently detected by TVR-PCR.

While most mapped telomeres are different, subsets of alleles can nevertheless be identified which have related internal structures (FIG. 6). These subsets of similar alleles usually share a common flanking haplotype, suggesting that they have diverged from a very recent common ancestral allele. Comparison of the most clearly aligned alleles, for example haplotype C alleles 142302 and 142308, suggest that most mutation events leading to telomere diversity involve the localised gain or loss of one or a few repeat units to create blocks of uniform repeat types. If true, this pattern of mutation is most likely supported by local replication slippage events involving one or a few repeat types.

Discussion

The frequency of base substitutional polymorphisms in non coding regions of the human genome is about 1 in 235 bases (Nickerson et al, 1992), although in a few regions, such as the HLA-DQA locus (Gyllensten and Erlich, 1988), the frequency of polymorphic sites is much higher. In the 850 bp adjacent to the Xp/Yp telomere we have identified a higher than average frequency of base substitutional polymorphisms (1 in 65 bp in Caucasians; 1 in 50 bp in Africans). However, there is almost complete linkage disequilibrium across polymorphic sites in the 850 bp and therefore only a small number of haplotypes within a population. Analysis of other clusters of biallelic polymorphisms in non-coding regions of the human genome has revealed multiple haplotypes, although partial linkage disequilibrium has been identified over short stretches of DNA sequence (Nickerson et al, 1992). Similarly some clusters of polymorphisms adjacent to minisatellites have shown partial linkage disequilibrium (Monckton et al, 1993). Partial linkage disequilibrium has been identified between an allele at a pseudoautosomal minisatellite (DXYS17) and the Y chromosome (Decorte et al, 1994) but the gradient of recombination across the pseudoautosomal region in the male germline may explain this association.

Strong linkage disequilibrium has been identified across 7 intragenic polymorphisms over 340 kbp of the Neurofibromatosis 1 region (Jorde et al, 1993), and between Y chromosome specific sequences and a polymorphism a few hundred bases into the pseudoautosomal region (Ellis et al., 1990). It is generally accepted that linkage disequilibrium can arise by admixture, genetic drift, selection or suppression of recombination but it is not clear which of these effects have influenced the establishment of strong linkage disequilibrium adjacent to the Xp/Yp telomere. There has been a high turnover of sequences at the ends of higher primate chromosomes during evolution (Royle et al., 1994) and our preliminary investigations suggest that the sequence organisation at the end of Xp/Yp and the location of the telomere is different in chimpanzees and gorillas compared with man. The sequence adjacent to the human Xp/Yp telomere has accumulated so many base substitutions that the haplotypes differ by as much as 1.8%; this suggests that the sequence is ancient but it does not explain the presence of nearly complete linkage disequilibrium across this region. One possible explanation is that a human progenitor contained a diverged duplication of the sequence containing the minisatellite and SINE elsewhere in the genome. A conversion between the two loci, and loss of the duplicated locus, could introduce a highly diverged haplotype adjacent to the XP/YP telomere and subsequent mutations would acculumulate indifferent haplotype lineages (such as those at the −217 and −826 position). However, our sequence data from a limited number of African and Caucasian DNAs homozygous for the flanking haplotypes show that the haplotypes are different in the two populations and therefore they may be diverging rapidly.

The close proximity of some of the polymorphic sites to the start of the Xp/Yp telomere repeat array has facilitated the development of telomere variant repeat mapping by PCR (TVR-PCR). The technique is similar to the method developed to map minisatellite alleles (MVR-PCR) (Jeffreys et al.; 1993) although the telomere and variant repeat primers are not 'tagged' with a non-complementary tail. Remarkable, allele-specific amplification can be achieved by TVR-PCR when the repeat primers are able to anneal at all 46 telomeres and the polymorphic site used for allele specific amplification lies within a SINE. Although this family of SINES has an estimated 20,000 copies in the genome (La Mantia et al.; 1989), sequence divergence between copies may reduce the number of possible annealing sites for the TS-30A primer within the genome. In addition, the likely absence of other copies of this family of SINEs close to any other telomere would explain the observed specific amplification from the Xp/Yp telomere.

TVR-PCR is a novel system for exploring allelic diversity in telomeres. The extreme allelic variation revealed at the proximal end of Xp/Yp telomeres in Caucasians suggest a high underlying mutation rate, although de novo mutants have yet to be identified. Comparison of closely related alleles suggests that the proximal end of the telomere repeat arrays more likely evolve by slippage, plus the occasional base substitution that introduces a novel variant repeat into the array. Strong association between related telomere maps and flanking haplotypes also suggest that telomeres are evolving largely along haploid lineages, consistent with an intra-allelic process such as slippage. The majority of mapped telomeres indicated that, in the germline at least, the proximal ends of telomeres are unperturbed by the activity of the enzyme, telomerase, that adds (TTAGGG) repeats onto the terminus of the telomere. However, there is Some indication that exchanges between different alleles have occurred. For example the telomere map 134114 associated with the flanking haplotype C is more similar to a subset of telomere maps assocated with the flanking haplotype B (for example 3502) than to other haplotype C alleles mapped to date; and the telomere map of 134901 associated with haplotype B is similar to other haplotype B associated telomeres but after 11 repeats the map becomes more similar to telomere maps, such as 4501, found in association with flanking haplotype C. It is not known whether such exchanges arise through inter-allelic recombination, or through a conversion-like process known to generate diversity at minisatellites. Whatever the basis of such exchanges, they cannot often involve recombination within the telomere-adjacent DNA since such exchanges would disrupt the strong linkage disequilbrium that exists.

TVR-PCR is a DNA typing system that may be useful in forensic DNA analysis, particularly for degraded DNA, when the interspersion patterns of the short repeat units could still be determined. TVR-PCR may be suitable for automation using fluorescent labelled flanking primers and typing on an automated sequencer. The technique could also be applied to studies of somatic turnover of telomeres in, for example senescing cell lines and it could in principal be developed for other human telomeres and for other species whose telomeres are composed of TTAGGG or similar repeats.

EXAMPLE =ps Materials and Methods

Genomic DNA's Caucasian DNAs lymphoblastoid DNAs from 80 unrelated individuals which constitute the parents of the CEPH (Centre d'Etude du Polymorphisme Humain) family DNAs. African and Afro-Caribbean DNAs were extracted from whole blood samples which had been collected in Great Britain. The Japanese DNA samples from whole blood were a gift from K. Tamaki (Jeffreys et al., 1991) and the Karitiana DNA samples were a gift from K. Kidd and F. Black.

Primers Primers described in this paper were synthesized on an Applied Biosystems 380B DNA synthesizer using reagents from Cruachem. The sequence of each primer is presented in Table 4(a) and 4(b).

PCR reactions All PCR reactions contained 1 $\mu$M of each primer in 45 mM Tris-HCl (pH 8.8 at 22° C.), 11 mM Ammonium sulphate, 4.5 mM $MgCl_2$, 6.7 mM 2-mercaptoethanol, 4.4 $\mu$M EDTA (pH 8.0), 113 gg/ml BSA, 1 mM of each dNTP and 2 units Taq polymerase (Advanced Biotechnology) (Jeffreys et al., 1991) unless otherwise stated and were cycled in a Perkin. Elmer 9600 thermal cycler.

Sequencing Genomic DNA (100 ng) was amplified with primers TSK8G and TSK8C or TSK8E and TSK8B or TSK8J and TSK8K in 20 $\mu$l volumes and the reactions were cycled 32 times at 96° C. 40 sec, 65° C. 50 sec, 70° C. 1 min. The products were purified by electrophoresis followed by electroelution onto a dialysis membrane and double stranded sequencing was carried out according to the method of Winship (Winship, 1989). A total of 803 bases were sequenced by this strategy.

Identification of the flanking—13 polymorchic position PCR products (approximately 500 bp) from the amplification of genomic DNA with TSK8E and TELG were gel purified and sequenced with the TSK8A primer as above. Allele specific amplification from DNAs heterozygous for A/B flanking haplotypes, prior to sequencing of B or C haplotypes, was achieved by amplification of genomic DNA with TSK8B to TSK8C at 96° C. 20 sec, 70° C. 2 mins 20 secs for 33 cycles. Allele specific amplification was verified by digesting a portion of the amplified products with Ddel; the remaining products were sequenced with primers TSK8B, TSK8E, TSK8G or TSK8C.

RFLP analysis of polymorphic positions −414, −427, −652 and −842 Genomic DNA was amplified with primers TSK8G and TSK8C in 20 $\mu$l. A fifth of the PCR reaction was digested to completion with the appropriate restriction enzyme for the polymorphic position (see Table 1) in a 16 $\mu$l reaction according to the manufacturer's instructions (Gibco-BRL) and in the presence of 1 mm spermidine trichloride. The products were resolved on a 2.2% Metaphor (FMC) agarose gel. RFLP analysis of the −176 position was achieved by amplification of genomic DNA in the presence of TSK8e (1 $\mu$M), TSK8B (0.5 $\mu$M) and TS-13AR (0.5 $\mu$M). The products were digested to completion with Ddel and the products resolved on a 4.5 Metaphor agarose gel. The polymorphism at −1888 was assayed by digestion of (TSK8J+TSK8K) PCR products with NlalV.

Haplotype analysis From polymorphic position −842: 4 $\mu$l of a 15 $\mu$l PCR amplification with TSK8E and the allele-specific primer TS-842C was digested to completion with the appropriate enzyme for the polymorphic position (−414, −427 and −652) and resolved as above.

RFLP analysis of the −176 position

PCR products from genomic DNA amplified with TSK8E and TSK8B were digested to completion (as above) with Ddel. Later PCR amplifications were carried out in the presence of primers TSK8e (1 $\mu$M), TSK8B (0.5 $\mu$M) and TS-13AR (0.5 $\mu$M) to complensate for the under-representation of A hallotype alleles in these reactions.

RFLP analysis of −1888 position Position −1888 was assayed by the digestion of PCR products amplified with TSK8J and TSK8K to completion (as above) with NlaIV.

ARMS assays for the −13 and −30 polymorphisms. The −13 polymorphism was identified during analysis of the −176 and −30 polymorphism because of inefficient amplification by the TSK8B primer. The −13 polymorphism was assayed using the allele-specific primer TS13AR with TSK8E. PCR reactions in the presence of TS13AR were cycled 32 times at 96° C. 50 sec, 66° C. 40 sec, 72° C. 1 min. Products were resolved in 1.5% HGT (FMC) agarose gels. The −30 polymorphism was assayed by PCR (10 µl) of genomic DNA in the presence of 1 µM of the allele specific primer TS-30A or TS-30TS in combination with 0.5 µM of both TSK8B and TS13AR primers. Reactions in the presence of TS-30A were cycled 32 times at 96° C. 15 sec, 62.5° C. 40 sec, 70° C. 30 sec. The products were resolved on a 4.5% Metaphor (FMC) agarose gel.

Two-state Telomere Variant Repeat Mapping The allele specific primer TS-13A was 5' end labelled in 10 µl reaction containing 0.5 µM primer, 50 mM Tris-HCl (pH7.6), 10 mM MgCl$_2$, 2 units T4 polynucleotide kinase, 370 kBq (g-$^{32}$P) ATP (Amersham International) at 37° C. for 2 hours. Two 10 µl PCR reactions containing 2 µl of the labelled primer and 0.1 µM of either TelH or TelG telomere repeat primers were cycled 19 times at 96° C. 20sec, 67° C. 40 sec, 70° C. 2 min. The products (6.5 µl) were resolved by electrophoresis on a standard 6% 0.5–2.5×TBE 7.67M urea polyacrylamide gel (Sequi-gen, Biorad) and a 5% 1×TBE 7.67M urea polyacrylamide extension gel and detected by autradiography.

Three-state Telomere Variant Repeat Mapping The flanking primer TS-30A was labelled as above. Genomic DNA (1 µg) was digested with AluI and DdeI according to manufacturer's instructions in a 10 µl reaction for 2 hours at 37° C. Neither of these enzymes cut between the TS-30A primer and the Xp/Yp telomere repeat array, and therefore this step eliminated the low level 'background' of products which had been misprimed by the TS-30A primer. The digested DNA (100 ng) was used in PCR reactions (as for two-state mapping) with the labelled flanking primer and either primer TelW, or TelX or TelY. Reactions with TelW were cycled 20 times at 96° C. 20 sec, 67° C. 40 sec, 70° C. 2 mins; reactions with TelX and TelY were cycled 19 times at 96° C. 20 sec, 68° C. 40 sec and 70° C. 2 mins. The products were resolved and detected as for two-state mapping.

Also the allele specification primers TS-30A or TS-30T were 5' end labelled in a 10 µl reaction containing 0.5 µM primer, 50 mM Tris-HCl (pH 7.6), 10 mM MgCl$_2$, 2 units T4 polynucleotide kinase, 370 kBq (g$^{32}$P) ATP (Amersham International) at 37° C. overnight. Genomic DNAs (1 µg) selected for telomere mapping were digested with AluI and DdeI in a 10 µl reaction for 2 hours at 37° C. These enzymes do not cut between the TS-30A/T priming site and the Xp/Yp telomere repeat array, and were used to eliminate the low level of "background" of products from mispriming by TS-30A or TS-30T. The digested DNA (100 ng) was used in each of three PCRs (10 µl) containing 2 µl of the labelled primer and 0.4 µM of TAG-TELW or TAG-TELX or TAG-TELY telomere repeat primers. Reactions in the presence of TAG-TELW and TAG-TELY were cycled 19 times at 96° C. 20 sec, 68° C. 40 sec and 70° C. 2 mins and reactions in the presence of TAG-TELX were cycled 19 times at 96° C. 20 sec, 67.5° C. 40 sec, 70° C. 2 mins. The products (6.5 µl) were resolved by electrophoresis in a 6% denaturing polyacrylamide 0.5–2.5×TBE buffer gradient gel containing 7.67M urea. 10×TBE contains 0.02M EDTA in 0.9M Tris-borate at pH8.3 5% polyacrylamide extension gels containing 1×TBE and 7.67M urea were used to resolve longer products. The products were detected by autoradiography.

Table 1

Polymorphisms in the DNA adjacent to the Xp/Yp telomere. The polymorphic positions are numbered from the telomere (right of the table) and the assays for the polymorphic sites analysed extensively are shown below. The top two rows of the table show the bases that occur at the polymorphic positions (5'>3'>telomere) in Caucasian and African DNAs. At the bottom of the table, the first column shows the haplotypes determined by analysis of the −414, −427, −652 and −842 positions. Full haplotypes across all the polymorphisms have been obtained from sequence analysis of 3 DNAs homozygous for haplotype A; and 3 for haplotype B from the CEPH panel; 3 African DNAs homozygous for the flanking haplotype A and 3 for flanking haplotype C. The haplotypes seem to be in very strong linkage disequilibrium within a population, but there are a number of differences between the A haplotypes of the Caucasian and African populations.

Table 2

Haplotypes formed from polymorphisms −414, −427, −652 and −842 at the Xp:Yp. pseudoautosomal telomere junction region.

Footnote: The haplotypes based on the assay of 4 polymorphic positions are in Hardy-Weinberg equilibrium in the populations tested (data now shown).

Table 2

Frequencies of haplotypes at the Xp/Yp pseudoautosomal telomere-junction and at the −1888 NlaIV polymorphism. Haplotypes A, B and C were determined by analysis of four polymorphic positions (−842, −652, −427 and −415). The frequency of the three haplotypes and the −1888 polymorphisms has been shown for each population; each polymorphism is in Hardy-Weinberg equilibrium in the populations tested (data not shown); n is the number of individuals tested for each population.

Table 3

Footnote: The −1888 polymorphism is in Hardy-Weinberg equilibrium in all the populations tested and preliminary data suggest that it is not in complete linkage disequilibrium with all the haplotypes adjacent to the telomere in the populations tested.

Table 3

Linkage disequilibrium between the flanking haplotypes of the Xp/Yp telomere and the −1888 polymorphic position in Caucasians The disequilibrium coefficients, D, for all allele combinations is shown. Duv=Puv−Puqv where Puv is the frequency of haplotype AuBv; Pv is the frequency of allele Av at the first locus and qv is the frequency of allele Bv at the second locus. D can vary between −0.25 and +0.25. The D values have been tested for significant deviation from random association using chi-squared statistics, *p, 0.05, * * * p<0.001. In an overall test for significant deviation of the D values from zero Total g$^2$=37.24 and with two degrees of freedom p<0.01. The linkage disequilibrium coefficients have also been converted to r values after standardisation for gene frequencies, r can vary between −1 and +1.

Table 4

Primer sequences. The non-complementary 5' tails (bold type) of primers TSK8C, TSK8E and TSK8G containing restriction sites (underlined) are shown. The repeat units of the telomere mapping primers TelH, TelG, TelW, TelY are bracketed underneath the sequence.

A. Diagram showing the distribution of polymorphic positions ▲, in the DNA adjacent to the Xp/Yp telomere, ▶, the SINE ▱ and the minisatellite, ///... the location of the PCR primers used in the analysis are show ➔, universal and allele specific prmers; ↳, primers including a non-complementary 5' tail).

B. Sequence of the DNA adjacent to the Xp/Yp telomere numbered from the first base (−1) adjacent to the first repeat of the telomere (GAGGG). The sequence of the minisatellite is shown as capital letters and the SINE in italics. The polymorphic positions are numbered above the sequence (−13 to −842) and the bases (bold type) at the polymorphic sites are shown. The restriction enzymes for the sites which create an RFLP are shown, and the 10 bp deleted in some African DNAs is underlined. The positions of the PCR primers are shown above (identical) or below (complementary) the sequence and * at the end of a primer represents a non-complementary 5' primer tail (see Table 4).

Figure 1C:
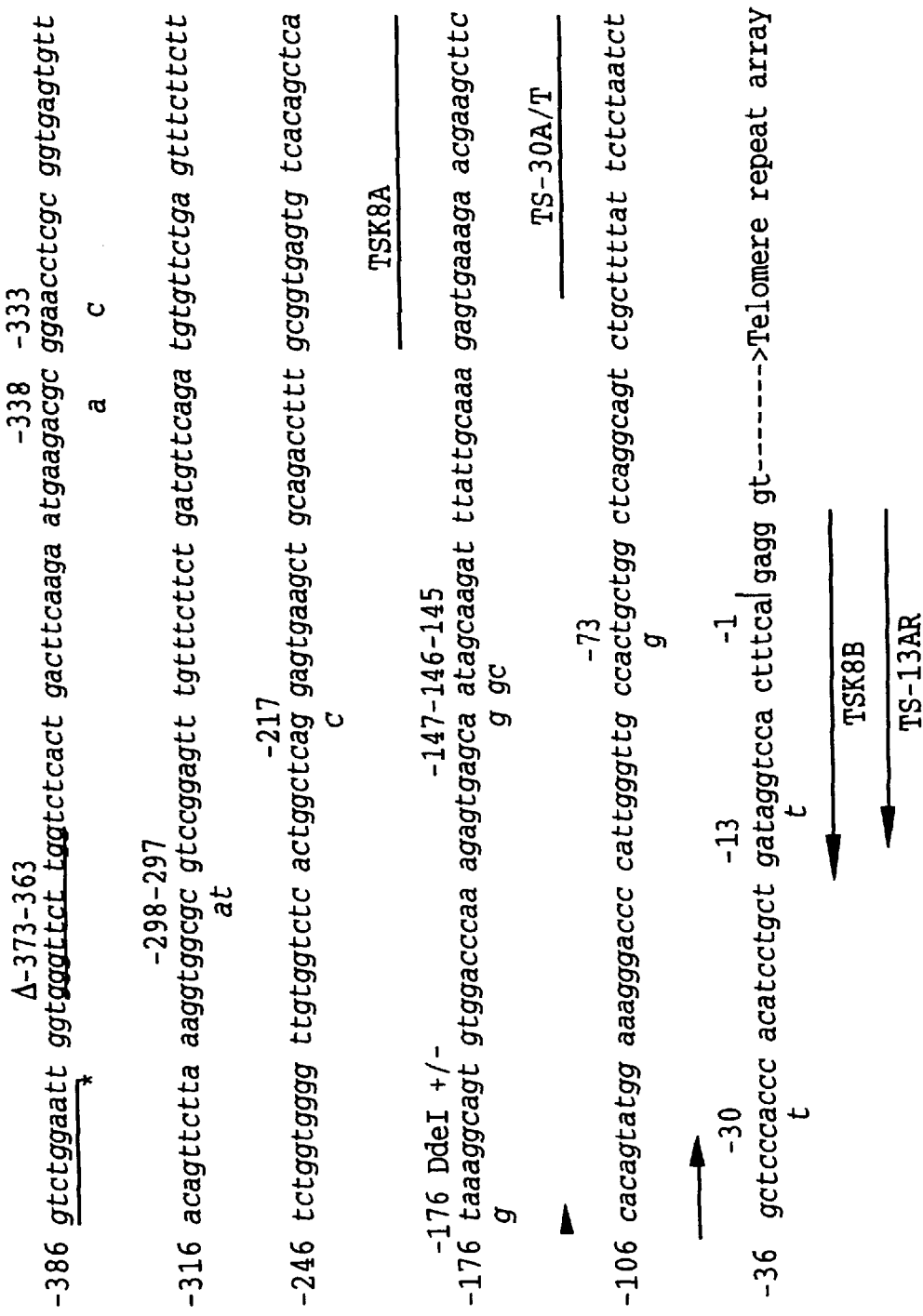
FIG. 1(a) Telomere Junction of the Xp/Yp Pseudoautosomal Region.

FIG. 1(b) and 1(c) Primer sequences for the DNA adjacent to the Xp/Yp telomere (SEQ ID NO:21)

Figure 2:
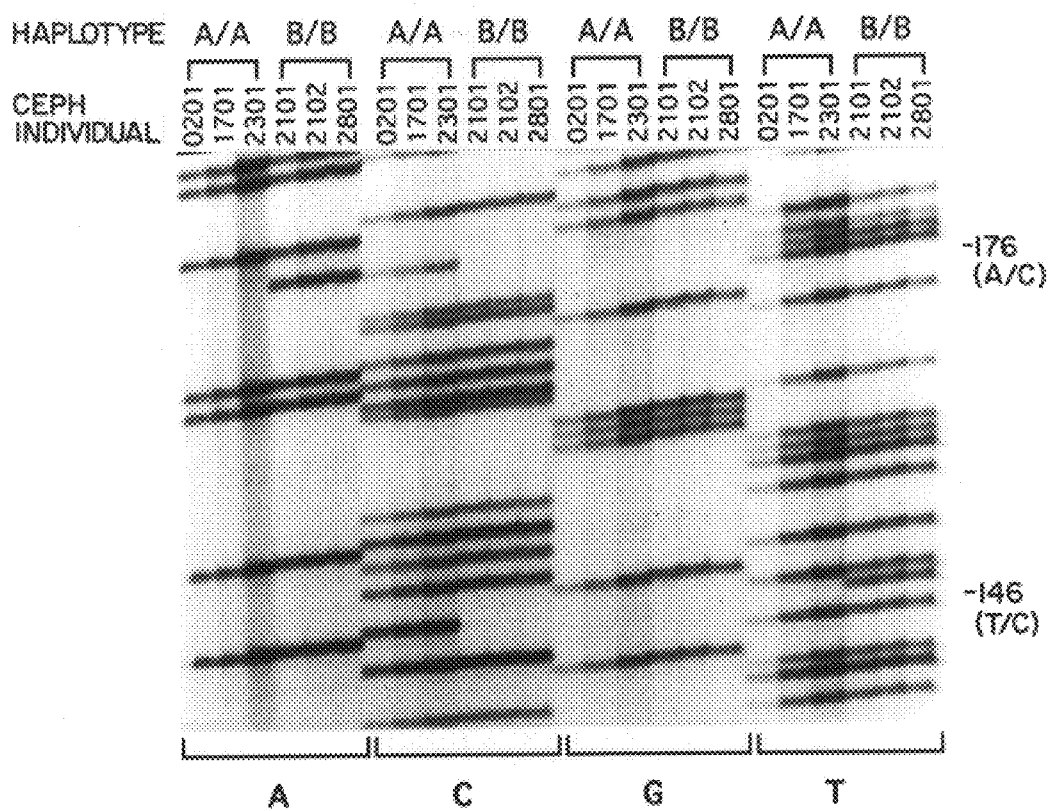

FIG. 2 Sequence polymorphisms found among Caucasian DNAs. Sequence from primer TSK8B of 3 CEPH parental DNAs (0201, 1701 and 2301) homozygous for flanking haplotype A and 3 CEPH parental DNAs (2101, 2102 and 2801) homozygous for flanking haplotype B is shown. At the positions −146 and −176 the DNAs homozygous for haplotype A have bases C and C and DNAs homozygous for haplotype B have bases T and A respectively. The −145 and −147 positions also shown in this figure are not polymorphic in Caucasians (see Table 1). The A-, C-, G- and T-tracks of all the samples have been run adjacent to one another to enhance the identification of the polymorphisms.

FIG. 3(a) Diagram showing the generation of telomere map. Allele-specific amplification is achieved in individuals heterozygous for the flanking haplotypes (AB or AC) from the −30 polymorphic position using a radioactively labelled primer TS-30A for amplification of alleles of haplotype B or C. Amplification from the variant (TGAGGG,▦) or telomere (TTAGGG,□), repeat types is achieved in separate reactions with primer Tel G (◀–) or Tel H (◀–). The products are resolved on a polyacrylamide gel, into ladders of bands based on a 6 bp repeat length. The two tracks can be read into a telomere code of T (TTAGGG) 7 1 t)and G(TGAGGG) N (null) repeat types. ▨, unknown repeat type.

FIG. 3(b) The principal of telomere map generation. Allele-specific amplification is achieved in individuals heterozygous for the flanking haplotypes (AB or AC) from the −30 polymorphic position using a radioactively labelled primer TS-30T or TS-30A for amplification of haplotype A or haplotype B and C alleles respectively. Amplification from the telomere TTAGGG □) or variant TGAGGG,▨, and TCAGGG,◪), repeat types is achieved in separate reactions with primers TAG-TELW (◀↳) TAG-TELX (◀↳) or TAG-TELY (◀↳). The products are resolved on a denaturing polyacrylamide gel into ladders of bands based on a 6 bp repeat unit length. The three tracks are read into a telomere code of T, TTAGGG, G, TGAGGG, C, TCAGGG and N, unknown repeat types.▨, -type repeat.

Figure 4:
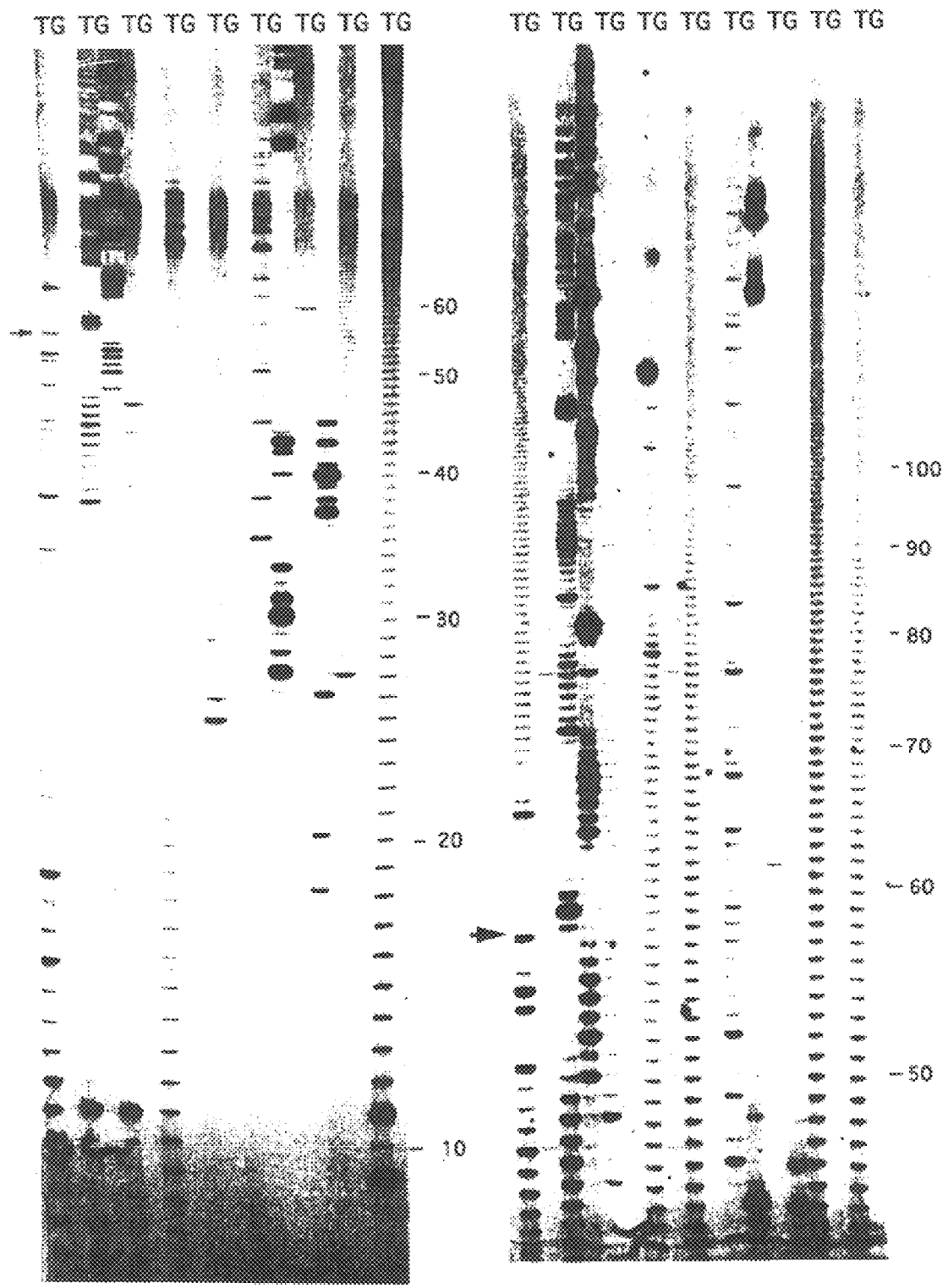
Figure 4A:
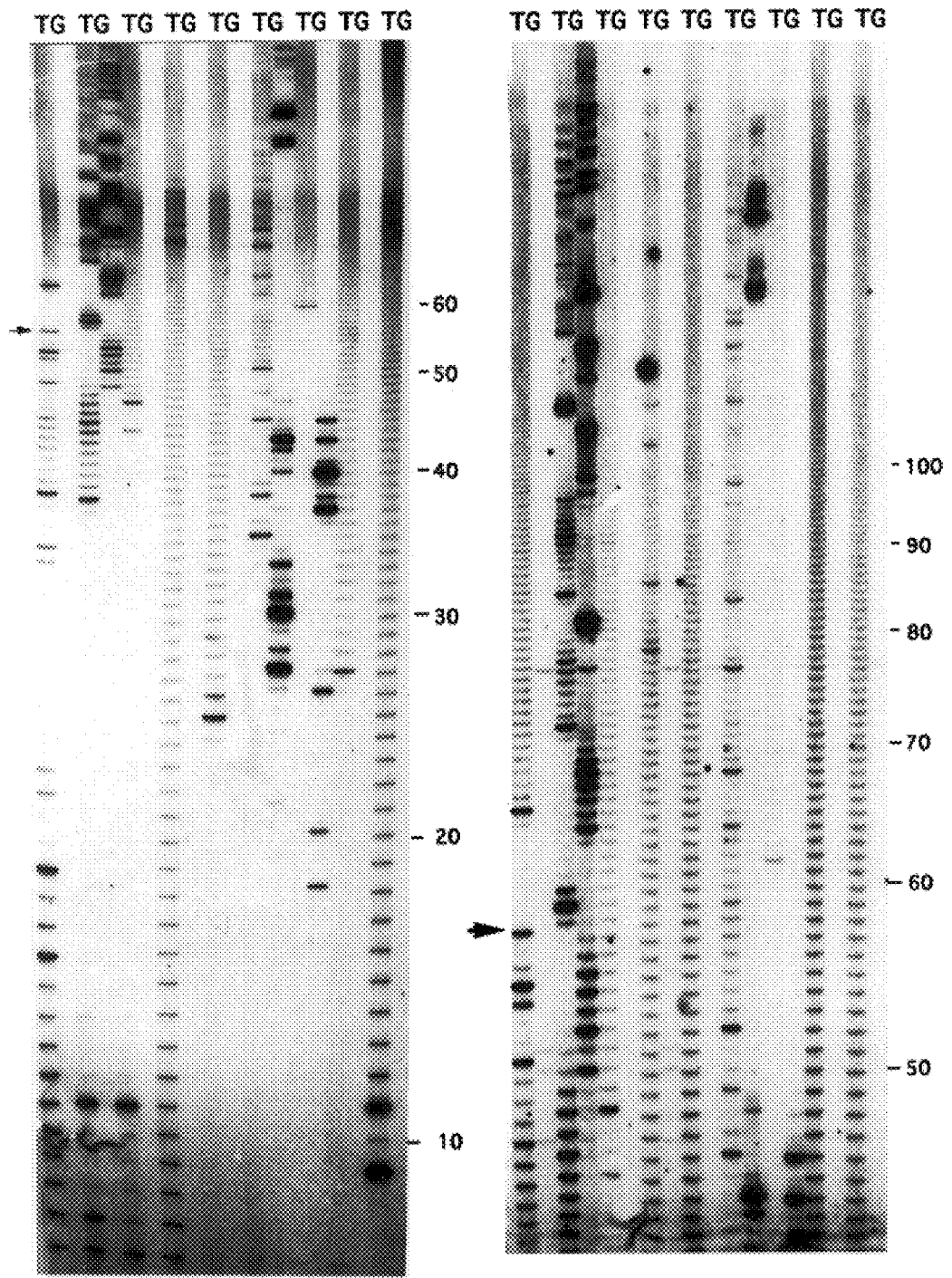

FIG. 4 Autoradiogram showing the telomere repeat maps from 9 alleles from unrelated individuals. A pair of adjacent T and G tracks represent a haploid telomere map and at 6 bp intervals a band is present in one or neither tracks. The distribution of T (TTAGGG), G (TGAGGG) and null (no band present) repeats can be read from the autoradiograms. The first repeat of the Xp/Yp telomere (GAGGGG)is read as a G-type and by combining the information from a standard and extension gel about 100 repeat units can be resolved. The arrow shows the overlap between the standard (left) and extension (right) gel and the scale shows the number of telomere repeats.

Figure 5A:
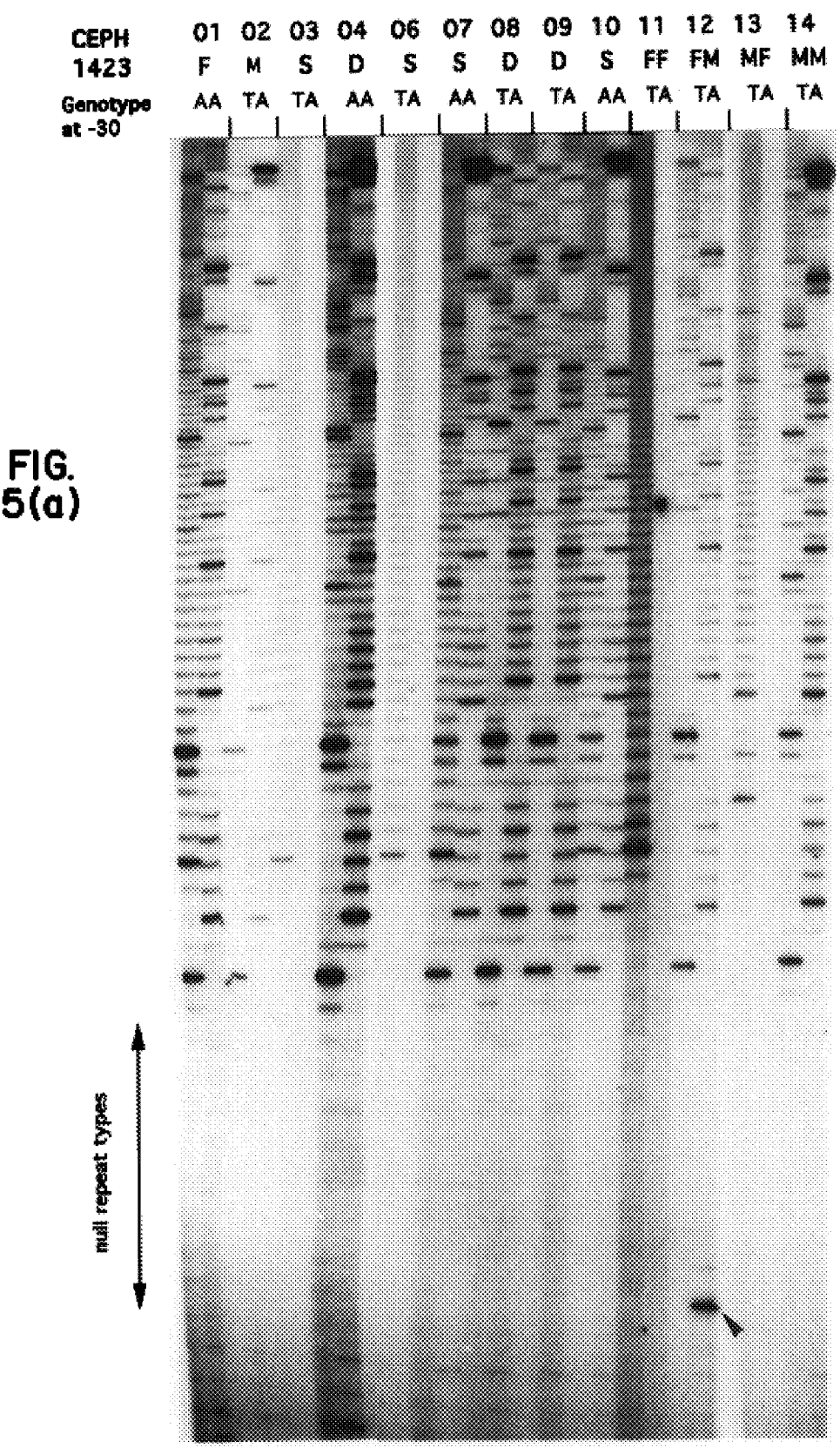

FIG. 5(a) Segregation of telomere maps within CEPH family 1423. All the grandparents (FF=11, FM=12, MF=13, MM=14) are heterozygous at the −30 position and amplification with the allele specific primer (TS-30A) generates a haploid telomere map from the chromosome with an A at the −30 position. Clearly the telomere map in the mother (M=02) who is also heterozygous at the −30 position, was inherited from her mother (MM=14), while the father (F=01) is homozygous at the −30 position, and has a diploid telomere map which is a composite of the telomere maps found in his father (FF=11) and mother (FM-12). However, FM's telomere map contains an additional (TGAGGG) repeat (arrowed) among null repeats which has not been inherited by the father or any of his children. Children (04, 07 and 10) are homozygous at the −30 position and therefore diploid codes are observed and children (03, 06, 08, and 09) are heterozygous for at the −30 position and have inherited a telomere map which can be amplified with the TS-30A primer from either their mother or father. The bases present at the −30 position are shown and the samples were loaded as T(TTAGGG) and G(TGAGGG) tracks as in FIG. 4.

Figure 5B:
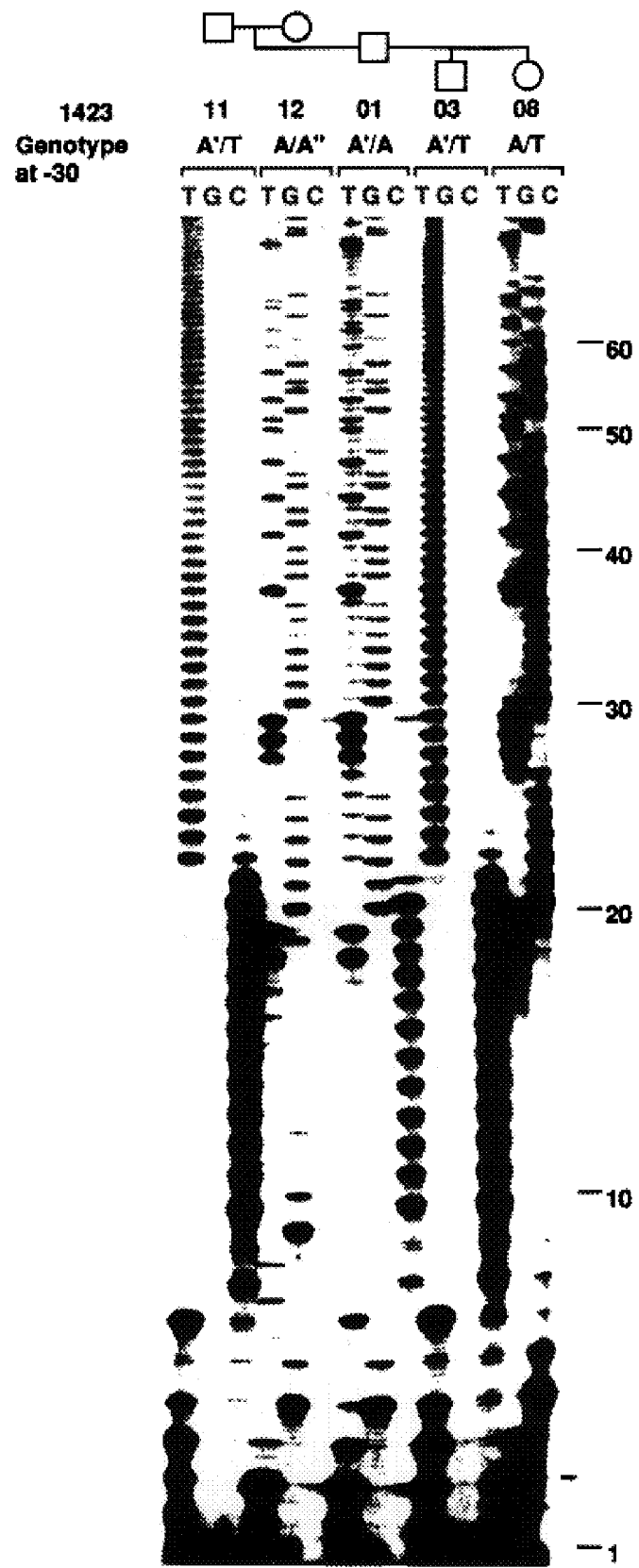

FIG. 5(b) Segregation of telomeres within a family. Telomere maps were generated using the TS-30A flanking primer from the grandfather (FF=11), grandmother (FM=12), father (F=01), son (S=03) and daughter (D=08) from the CEPH 1423 family. The grandfather was heterozygous (AT) at the −30 positon and a haploid telomere map (A') was produced. The grandmother was homozygous (AA) at the −30 position and therefore a diploid telomere pattern was produced from the combined maps of telomeres designated A and A". The father was also homozygous at the −30 position and produced a diploid telomere pattern, from the A' and A telomeres in his parents. The two children were both heterozygous at the −30 position, the son has inherited the A' telomere from his father while the daughter inherited the A telomere map. Each telomere is deduced from three tracks (T, G and C) for the distribution of TTAGGG, TGAGGG and TCAGGG repeat types respectively.

FIG. 6 Three-state telomere variant repeat maps and codes.

(a) Telomere maps from five CEPH DNAs (6602, 1702, 3502, 3701 and 6601), all heterozygous at the flanking −30 position, were generated by amplification between the labelled flanking primer TS-30A and either TelW, or TelX, or TelY which primes from T (TTAGGG), or G(TGAGGG), or C (TCAGGG) repeat types respectively. The reactions were resolved in adjacent tracks labelled T, G, C, on a denaturing polyacrylamide gel. The scale on the right shows the number of repeat units.

Figure 6A:
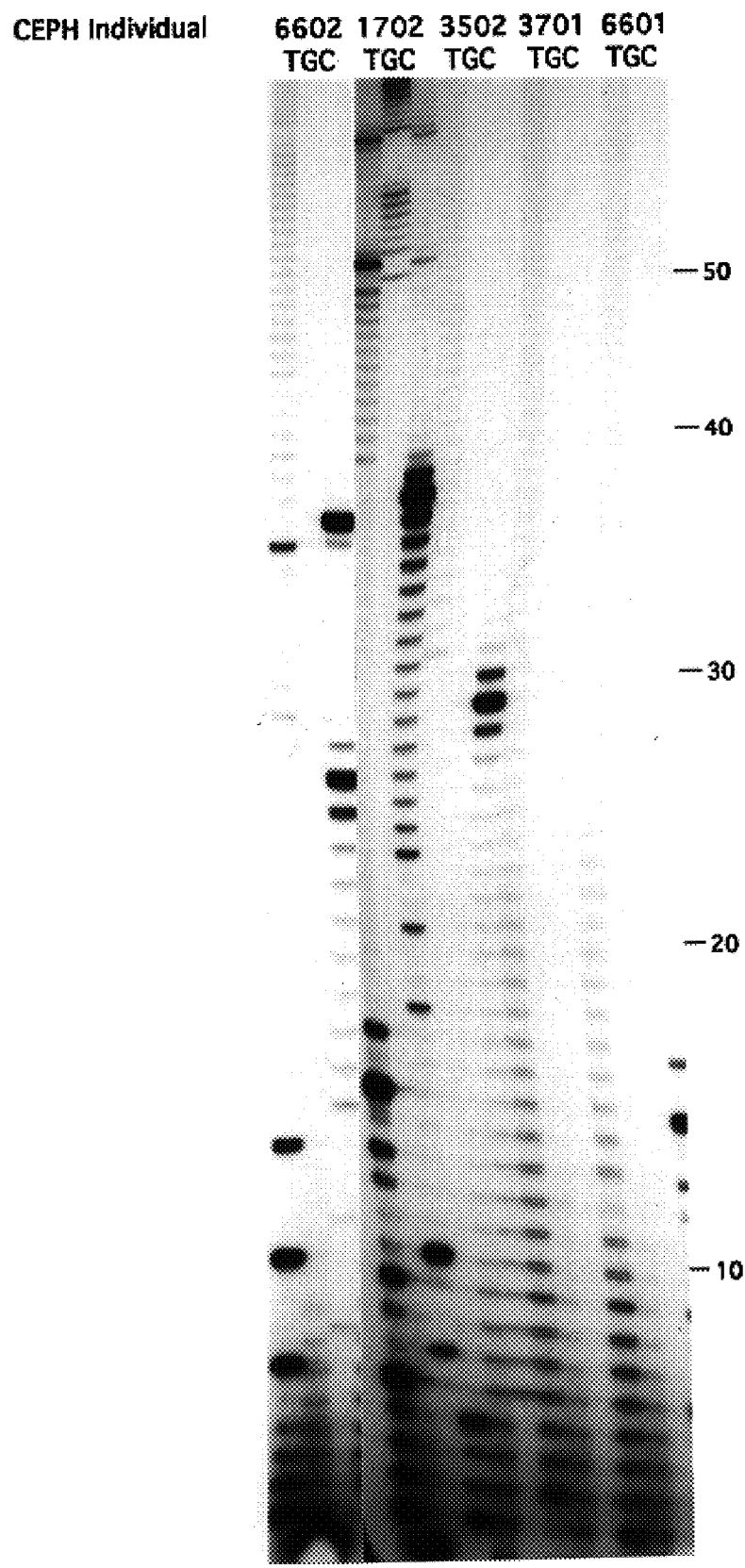
Figure 6C:
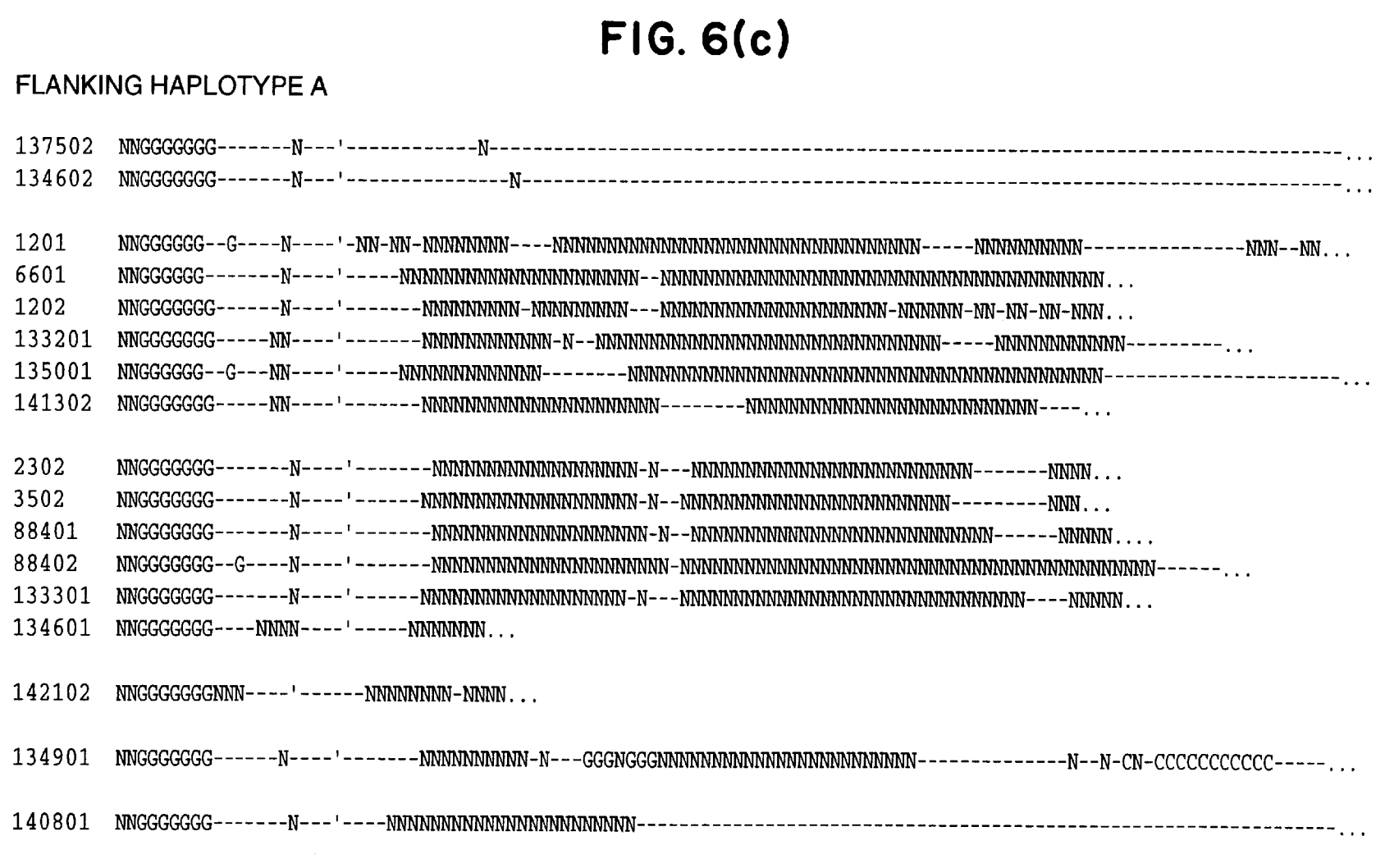

(b) The three-stated telomere variant repeat maps shown in FIG. 6A have been coded for database analysis. the presence of a band in one of the three tracks for each DNA sample was scored as a T, G or C repeat type. Occasionally a band appears in the T and C tracks at the same position in which case it is scored as a T type repeat unit. No band present in any of the tracks was scored as an N or null repeat type. Some imperfections still exist in the three-stated TVR-PCR technology, for example the presence of doublets instead of single bands at each position in the ladder; the TelX (TGAGGG) primer generated a non-specific background for the first 10 to 15 repeats and it was ignored when a telomere code was read; the bands at the end of a block of repeat units of one type tended to be darker than the others.

(f) Hypervariability of proximal Xp/Yp telomere arrays. Single allele telomere maps, obtained from the indicated CEPH individuals heterozygous at the −30 flanking polymorphism were coded for the distribution of T, (TTAGGG), G (TGAGGG), C (TCAGGG) and N (unknown) repeat types. The telomere maps obtained from 65 telomeres have been grouped according to their flanking haplotype. Haplotype A alieles have nucleotide T at the −30 position and were amplified by the TS-30T primer whereas haplotypes B and C have nucleotide A at the −30 and were amplified by the TS-30A primer. All except one of the haplotype B and C telomeres begin with a G-type repeat. The unknown sequence at the beginning of the haplotype A telomeres is represent by two N-type repeats. A prime (') has been introduced to indicate a minor change in the 6 bp periodicity of some telomere maps.

Table 1.
Polymorphisms in the DNA adjacent to the Xp/Yp telomere. The polymorphic positions are numbered from the telomere (right of the table) and the assays for the polymorphic sites analysed extensively are shown below. The top two rows of the table show the bases that occur at the polymorphic positions (5'→3'→telomere) in Caucasian and African DNAs. At the bottom of the table, the first column shows the haplotypes determined by analysis of the −414, −427, −652 and −842 positions. Full haplotypes across all the polymorphisms have been obtained from sequence analysis of 3 DNAs homozygous for haplotype A; and 3 for haplotype B from the CEPH panel; 3 African DNAs homozygous for the flanking haplotype A and 3 for flanking haplotype C. The haplotypes seem to be in very strong linkage disequilibrium within a population, but there are a number of differences between the A haplotypes of the Caucasian and African populations.

Table 2.
Footnote: The haploytpes based on the assay of 4 polymorphic positions are in Hardy-Weinberg equilibrium in the populations tested (data not shown).

Table 3.
Footnote: The −1888 polymorphism is in Hardy-Weinberg equilibrium in all the populations tested and preliminary data suggest that it is not in complete linkage disequilbrium with all the haplotypes adjacent to the telomere in the populations tested.

Table 4.
Primer sequences. The non-complementary 5' tails (bold type) of primers TSK8C, TSK8E and TSK8G containing restriction sites (underlined) are shown. The repeat units of the telomere mapping primers TelH,TelG, TelW, TelX, TelY are bracketed underneath the sequence.

TABLE 1

| position from first telomere repeat | −842 DdeI +/− | −652 AvaII +/− | −554 | −544 | −540 | ←TSK8G TSK8E→ −427 TaqI +/− | −414 MboII +/− | Δ 373–363[a] | −338 |
|---|---|---|---|---|---|---|---|---|---|
| Nucleotides at the polymorphic positions 5' → 3' → telomere. | | | | | | | | | |
| Caucasian | C/A | G/A | A/T | G/C | T/C | G/A | C/T | + | G |
| African | C/A | G/A | A | G/C | T/C | G/A | C/T | +/− | A/G |

| position from first telomere repeat | −333 | −298 | −297 | ←TSK8G TSK8E→ −176 DdeI +/− | −147 | −146 | −145 | −73 | −30 ARMS | −13 ARMS |
|---|---|---|---|---|---|---|---|---|---|---|
| Nucleotides at the polymorphic positions 5' → 3' → telomere. | | | | | | | | | | |
| Caucasian | A | A/G | T/C | G/T | A | G/A | T | C | T/A | T/A |
| African | C/A | A/G | T/C | G/T | G/A | G | C/T | G/C | T/A | not tested |

| position from first telomere repeat | −842 DdeI +/− | −652 AvaII +/− | −554 | −544 | −540 | ←TSK8G TSK8E→ −427 TaqI +/− | −414 MboII +/− | Δ 373–363[a] | −338 |
|---|---|---|---|---|---|---|---|---|---|
| Haplotypes from sequence analysis. | | | | | | | | | |
| CEPH Haplotypes | | | | | | | | | |
| A | C | G | A | G | T | G | C | + | G |
| B | A | A | T | C | C | A | T | + | G |
| C | A | A | | | | G | T | | |

TABLE 1-continued

African Haplotypes

| | | | | | | | | | | |
|---|---|---|---|---|---|---|---|---|---|---|
| A | C | G | A | C (AFC = C/O) | C (AFC = T/C) | G | C | – | A | |
| B | | A | A | | | A | T | | | |
| C | | A | A | A | G (AFC = C/O) | T (AFC = T/C) | G | T | + | G |

| | | | | ←TSK8G TSK8E→ | | | | | | |
|---|---|---|---|---|---|---|---|---|---|---|
| position from first telomere repeat | –333 | –298 | –297 | –176 DdeI +/– | –147 | –146 | –145 | –73 | –30 ARMS | –13 ARMS |

Haplotypes from sequence analysis.

CEPH Haplotypes

| | | | | | | | | | | |
|---|---|---|---|---|---|---|---|---|---|---|
| A | A | A | T | G | A | G | T | C | T | T |
| B | A | G | C | T | A | A | T | C | A | A |
| C | | | | | | | | | A | |

African Haplotypes

| | | | | | | | | | | |
|---|---|---|---|---|---|---|---|---|---|---|
| A | C | A | T | G | G | G | C | G | not tested | not tested |
| B | | | | | | | | | | |
| C | A | G | C | T | A | G | T | C | not tested | not tested |

*The 10 bases between –363 and –373 are present (+) or absent (–) as indicated.

TABLE 2

Haplotypes formed from polymorphisms –414, –427, –652 & –842 at the Xp:Yp pseudoautosomal telomere junction region

| Haplotype | –842 | –652 | –427 | –414 |
|---|---|---|---|---|
| A | C | G | G | C |
| B | A | A | A | T |
| C | A | A | G | T |

| | Caucasians | | Japanese | | Africans | | Afro-Caribbeans | | Karitiano | |
|---|---|---|---|---|---|---|---|---|---|---|
| Genotype | Observed | Expected | Observed | Expected | Observed | Expected | Observed | Expected | Observed | Expected |
| A/A | 22 | 20.5 | 11 | 8.6 | 17 | 15.8 | 22 | 19.7 | 0 | 0.0 |
| A/B | 33 | 35.9 | 38 | 42.6 | 1 | 0.8 | 3 | 8.0 | 0 | 0.0 |
| A/C | 4 | 4.1 | 0 | 0.3 | 7 | 9.8 | 7 | 6.6 | 0 | 0.0 |
| B/B | 17 | 15.8 | 55 | 52.9 | 0 | 0.0 | 4 | 0.8 | 22 | 22.0 |
| B/C | 4 | 3.6 | 1 | 0.7 | 0 | 0.2 | 0 | 1.3 | 0 | 0.0 |
| C/C | 0 | 0.2 | 0 | 0.0 | 3 | 1.5 | 1 | 0.5 | 0 | 0.0 |
| Total | 80 | | 105 | | 28 | | 37 | | 22 | |

| Frequencies | | Frequencies | | Frequencies | | Frequencies | | Frequencies | | |
|---|---|---|---|---|---|---|---|---|---|---|
| A = | 0.506 | | 0.286 | | 0.750 | | 0.730 | | 0.000 | |
| B = | 0.444 | | 0.710 | | 0.018 | | 0.149 | | 1.000 | |
| C = | 0.050 | | 0.005 | | 0.232 | | 0.122 | | 0.000 | |
| Observed Heterozygosity = | | 51 | | 37 | | 29 | | 27 | | 0 |

TABLE 3

Genotype frequencies at the −1888 polymorphism

| −1888 A/G | | | | | | | | Nla IV +/− | | | |
|---|---|---|---|---|---|---|---|---|---|---|---|
| Caucasians | | | Japanese | | | Africans | | | Afro-Caribbean | | |
| Genotype | Observed | Expected | Genotype | Observed | Expected | Genotype | Observed | Expected | Genotype | Observed | Expected |
| +/+ | 30 | 25.88 | +/+ | 7 | 5.14 | +/+ | 3 | 3.34 | +/+ | 10 | 6.49 |
| +/− | 31 | 39.24 | +/− | 32 | 35.73 | +/− | 13 | 12.31 | +/− | 11 | 18.01 |
| −/− | 19 | 14.88 | −/− | 64 | 62.14 | −/− | 11 | 11.34 | −/− | 16 | 12.49 |
| Total | 80 | | Total | 103 | | Total | 27 | | Total | 37 | |
| Allele | freq | | Allele | freq | | Allele | freq | | Allele | freq | |
| + | 0.57 | | + | 0.22 | | + | 0.35 | | + | 0.42 | |
| − | 0.43 | | − | 0.78 | | − | 0.65 | | − | 0.58 | |
| Heterozygosity % = | | 49 | Heterozygosity % = | | 35 | Heterozygosity % = | | 46 | Heterozygosity % = | | 49 |
| Chi-Squared = | | 3.53 | Chi-Squared = | | 1.12 | Chi-Squared = | | 0.08 | Chi-Squared = | | 5.61 |
| (2df) p > | | 0.1 | (2df) p > | | 0.5 | (2df) p > | | 0.9 | (2df) p > | | 0.05 |

TABLE 4

Primers for PCR

| | | |
|---|---|---|
| TSK8A (SEQ ID NO: 1): | 5'-GAGTGAAAGAACGAAGCTTC-3' | |
| TSK8B (SEQ ID NO: 2): | 5'-CCCTCTGAAAGTGGACCTAT-3' | |
| TSK8C (SEQ ID NO: 3): | 5'-GC<u>GGTACC</u>AGGGACCGGGACAAATAGAC-3'<br>KpnI | |
| TSK8E (SEQ ID NO: 4): | 5'-GC<u>GGTACC</u>TAGGGGTTGTCTCAGGGTCC-3'<br>KpnI | |
| TSK8G (SEQ ID NO: 5): | 5'-CG<u>GAATTC</u>CAGACACACTAGGACCCTGA-3'<br>EcoRI | |
| TSK8J (SEQ ID NO: 6): | 5'-GAATTCCTGGGGACTGCGGATG-3' | (−2000) |
| TSK8K (SEQ ID NO: 7): | 5'-CATCCCTGAAGAAGCATCTTGGCC-3' | (−1500) |

Allele Specific Primers.

| | |
|---|---|
| TS-842C (SEQ ID NO: 8): | 5'-AGACGGGGACTCCCGAGC-3' |
| TS-30A (SEQ ID NO: 9): | 5'-CTGCTTTTATTCTCTAATCTGCTCCCA-3' |
| TS-30TS (SEQ ID NO: 10): | 5'-CTTTTATTCTCTAATCTGCTCCCT-3' |
| TS-30T (SEQ ID NO: 22): | 5'-CTGCTTTTATTCTCTAATCTGCTCCCT-3' |
| TS-13AR (SEQ ID NO: 11): | 5'-ACCCTCTGAAAGTGGACCA-3' |

Primers for telomere mapping

Two state mapping:

TelH (SEQ ID NO: 12): 5'-CCCTAACCCTAACCCTAACCCTA-3'

TelG (SEQ ID NO: 13): 5'-CCCTCACCCTCACCCTCACCCTC-3'

Three state mapping:

TelW (SEQ ID NO: 14): 5'-CCCTTACCCTTACCCTNACCCTA-3'

TelX (SEQ ID NO: 15): 5'-CCCTTACCCTTACCCTNACCCTC-3'

TelY (SEQ ID NO: 16): 5'-CCCTTACCCTTACCCTNACCCTG-3'

What is claimed is:

1. A method of characterising a test sample of genomic DNA which comprises
   contacting the test sample with at least one type specific primer to prime selectively, within a telomere repeat array, internal repeat units of one type, and
   extending the type specific primer in the presence of appropriate nucleoside triphosphates and an agent for polymerisation to produce a set of amplification products extending from the internal repeat units of that one type to at least the end of the telomere repeat array, and determining genetic variation of the telomere repeat array by the sizes of the set of amplification products;
   wherein a type specific primer comprises at least one sequence selected from the group consisting of
   Te1H (SEQ ID NO:12) 5'-CCCTAACCCTAACCCTAACCCTA-3',
   Te1G (SEQ ID NO:13) 5'-CCCTCACCCTCACCCTCACCCTC-3',
   Te1W (SEQ ID NO:14) 5'-CCCTTACCCTTACCCTNACCCTA-3',
   Te1X (SEQ ID NO:15) 5'-CCCTTACCCTTACCCTNACCCTC-3', and
   Te1Y (SEQ ID NO:16) 5'-CCCTTACCCTTACCCTNACCCTG-3';
   thereby characterising the test sample of genomic DNA.

2. A method as claimed in claim 1 wherein two or more different type specific primers are used to generate different sets of amplification products optionally having different labels.

3. A method as claimed in claim 1 wherein an amplification product extends to a locus flanking the telomere repeat array and acts as a template for a common primer which is optionally labelled and which hybridises to the flanking locus; and wherein said method further comprises adding said common primer and extending said common primer in the presence of appropriate nucleoside triphosphates and an agent for polymerisation to amplify the set of amplification products.

4. A method as claimed in claim 3 wherein type specific primer extension and common primer extension are repeated in a polymerase chain reaction.

5. A method as claimed in any one of claims 3–4 wherein the flanking locus is polymorphic and the common primer is an allele specific primer.

6. A method as claimed in claim 1 wherein two or more types of telomere internal repeat units are analysed.

7. A method as claimed in claim 3 wherein the type specific primer and/or the common primer have a tail sequence which hybridizes with a tail specific primer.

8. A method as claimed in claim 3 wherein the type specific primer and/or the common primer are fluorescently end-labelled.

9. A method as claimed in claim 1 wherein the telomere repeat array is in the Xp/Yp pseudoautosomal region (PAR1).

10. A method as claimed in claim 3 wherein the flanking locus is in a minisatellite region.

11. A method as claimed in claim 3 wherein the telomere repeat array is in a short interspersed repetitive element (SINE).

12. A method of characterising a test sample of genomic DNA which comprises contacting the test sample with an allele specific primer to prime selectively at one or more polymorphic loci within twenty kilobases of the Xp/Yp pseudoautosomal region (PAR1) telomere repeat array, extending the allele specific primer in the presence of appropriate nucleoside triphosphates and an agent for polymerisation, and detecting allelic variants by the presence or absence of the allele specific primer extension product; thereby characterising the test sample of genomic DNA.

13. A method as claimed in claim 12 in which the primer extension product of one allele specific primer can act as the template for an allele specific primer for a different polymorphic locus in a polymerase chain reaction.

14. A method as claimed in claim 3 wherein the common primer is an allele specific primer which primes selectively at one or more polymorphic loci at a position selected from the group consisting of positions −13, −30, and −176 as determined from the end of the Xp/Yp pseudoautosomal region (PAR1) telomere repeat array.

15. A PCR primer comprising at least one sequence selected from the group consisting of:
   TSK8A (SEQ ID NO:1) 5'-GAGTGAAAGAACGAAGCTTCC-3',
   TSK8B (SEQ ID NO:2) 5'-CCCTCTGAAAGTGGACCTAT-3',
   TSK8C (SEQ ID NO:3) 5'-GCGGTACCAGGGACCGGGACAAATAGAC-3',
   TSK8E (SEQ ID NO:4) 5'-GCGGTACCTAGGGGTTGTCTCAGGGTCC-3',
   TSK8G (SEQ ID NO:5) 5'-CGGAATTCCAGACACACTAGGACCCTGA- 3',
   TSK8J (SEQ ID NO:6) 5'-GAATTCCTGGGGACTGCGGATG-3', and
   TSK8K (SEQ ID NO:7) 5'-CATCCCTGAAGAAGCATCTTGGCC-3'.

16. An allele specific primer comprising at least one sequence selected from the group consisting of:
   TS-842C (SEQ ID NO:8) 5'-AGACGGGGACTCCCGAGC-3',
   TS-30A (SEQ ID NO:9) 5'-CTGCTTTTATTCTCTAATCTGCTCCA-3',
   TS-30TS (SEQ ID NO:10) 5'-CTTTTATTCTCTAATCTGCTCCCT-3',
   TS-13AR (SEQ ID NO:11) 5'-ACCCTCTGAAAGTGGACCA-3', and
   TS-30T (SEQ ID NO:22) 5'-CTGCTTTTATTCTCTAATCTGCTCCCT-3'.

17. A type specific primer comprising at least one sequence selected from the group consisting of:
   TAG-Te1W (SEQ ID NO:18) 5'-TCATGCGTCCATGGTCCGGACCCTTACCCTTA CCCTNACCCTA-3',
   TAG-Te1X (SEQ ID NO:19) 5'-TCATGCGTCCATGGTCCGGACCCTTACCCTTA CCCTNACCCTC-3', and TAG-Te1Y (SEQ ID NO:20)
5'-TGATGCGTCCATGGTCCGGACCCTTACCCTTA
CCCTNACCCTG-3'.

18. A method according to claim 3, wherein said method is carried out using a test kit to characterize a test sample of genomic DNA, said test kit comprising one or more member selected from the group consisting of a type specific primer, an allele specific primer and a common primer.

19. A method for determining genetic linkage between a telomere polymorphism and another polymorphism, said method comprising the steps of characterising a test sample of genomic DNA by the process of claim 1, wherein the sizes of the amplification products represents a telomere polymorphism, and determining whether the telomere polymorphism is genetically linked to said another polymorphism.

20. A method for determining genetic linkage between a telomere polymorphism and another polymorphism, said method comprising the steps of characterising a test sample of genomic DNA by the process of claim 3, wherein the sizes of the amplification products represents a telomere polymorphism, and determining whether the telomere polymorphism is genetically linked to said another polymorphism.

21. A method for determining genetic linkage between a PAR1 polymorphism and another polymorphism comprising the steps of characterising a test sample of genomic DNA by the process of claim 12, wherein the presence or absence of the allele specific primer extension product represents a PAR1 polymorphism, and determining whether the PAR1 polymorphism is genetically linked to said another polymorphism.

22. A method for identifying an individual or determining family relationships from one or more samples of genomic DNA, comprising the steps of characterising at least one test sample of genomic DNA according to the process of claim 1 and comparing the characteristic of the test sample from the individual with the characteristic of the test sample from other individuals or members of the family, respectively, to identify the individual as being a member of the family or not.

23. A method as claimed in claim 1, wherein the test sample is from a human.

24. A method as claimed in claim 1, wherein the test sample is from a non-human organism and the genomic DNA sequence contains TTAGGG and variant telomere repeat types.

25. A method as claimed in claim 1, wherein said at least one type specific primer primes selectively in a repeat unit selected from the group consisting of TTAGGG, TTGGGG, and TGAGGG, wherein the repeat unit is a type of internal repeat unit within the telomere repeat array.

26. A method as claimed in claim 1 wherein the sizes of the set of amplification products are less than 1000 bases.

27. A method as claimed in claim 1 wherein the sizes of the set of amplification products are less than 600 bases.

28. A method of determining genetic polymorphism of a telomere repeat array in genomic DNA, wherein the telomere repeat array is comprised of an internal repeat unit of two or more different types, comprising:
(a) hybridizing at least one type specific primer with the genomic DNA such that the type specific primer hybridizes to the internal repeat unit of one type,
(b) initiating synthesis of a type specific extension product from the type specific primer,
(c) extending the type specific primer to synthesize the type specific extension product which extends from the internal repeat unit of one type to at least an end of the telomere repeat array, and
(d) amplifying the type specific extension product to produce an amplification product;
wherein a type specific primer comprises at least one sequence selected from the group consisting of
Te1H (SEQ ID NO:12)
5'-CCCTAACCCTAACCCTAACCCTA-3',
Te1G (SEQ ID NO:13)
5'-CCCTCACCCTCACCCTCACCCTC-3',
Te1W (SEQ ID NO:14)
5'-CCCTTACCCTTACCCTNACCCTA-3',
Te1X (SEQ ID NO:15)
5'-CCCTTACCCTTACCCTNACCCTC-3', and
Te1Y (SEQ ID NO:16)
5'-CCCTTACCCTTACCCTNACCCTG-3';
wherein size of the amplification product determines genetic polymorphism of the telomere repeat array.

29. A method as claimed in claim 28, wherein each of the internal repeat units of one type is located at a different position in the telomere repeat array, the type specific primer hybridizes to each internal repeat unit of one type, and further comprising:
(e) synthesizing a set of type specific extension products from the internal repeat units of one type, wherein each type specific extension product is synthesized from a related internal repeat unit of one type, and
(f) amplifying the set of type specific extension products to produce a set of amplification products of one type, wherein each amplification product of one type has a different size depending on the position of the related internal repeat unit of one type in the telomere repeat array;
wherein sizes of the set of amplification products of one type determine genetic polymorphism of the telomere repeat array.

30. A method as claimed in claim 28 further comprising separating the set of amplification products of one type to form a sample code for the genomic DNA.

31. A method as claimed in any one of claims 28–29 further comprising hybridization, initiation of synthesis, extension, and amplification with a second type specific primer such that two different types of amplification products are produced.

32. A method as claimed in claim 28 wherein the genetic polymorphism of the telomere repeat array is determined by repetition of the internal repeat unit in the telomere repeat array.

33. A method as claimed in claim 28 wherein the genetic polymorphism of the telomere repeat array is determined by identification of the type of internal repeat unit in the telomere repeat array.

34. A method as claimed in claim 28 wherein the internal repeat unit is selected from the group consisting of TTAGGG, TTGGGG, and TGAGGG.

35. A method as claimed in claim 28 wherein the type specific extension product extends to a locus flanking the telomere repeat array and further comprising:
(d) hybridizing a common primer with the type specific extension product, wherein the common primer is able to hybridize to the flanking locus, and
(e) extending the common primer to synthesize the common extension product.

36. A method as claimed in claim 35 wherein type specific primer extension and common primer extension are repeated in a polymerase chain reaction to amplify complementary type specific extension product and common extension product.

37. A method as claimed in any one of claims 35–36 wherein the flanking locus is polymorphic and the common primer is an allele specific primer.

38. A method as claimed in claim 28 wherein the type specific extension product is amplified in a polymerase chain reaction.

39. A method as claimed in claim 28 wherein the type specific primer hybridizes to the internal repeat unit of one type, and initiates synthesis within each internal repeat unit of one type.

40. A method as claimed in claim 28 wherein the size of the amplification product is less than 1000 bases.

41. A method as claimed in claim 28 wherein the size of the amplification product is less than 600 bases.

42. A method of characterising a test sample of genomic DNA which comprises contacting the test sample with an allele specific primer to prime selectively at one or more polymorphisms at a position selected from the group consisting of positions −13, −30, −73, −145, −146, −147, −176, −297, −298, −333, −338, a deletion from −363 to −373, −414, −415, −427, −540, −554, −652, and −842 as determined from the end of the Xp/Yp pseudoautosomal region (PAR1) telomere repeat array, extending the allele specific primer in the presence of appropriate nucleoside triphosphates and an agent for polymerisation, and detecting allelic variants by the presence or absence of the allele specific primer extension product; thereby characterising the test sample of genomic DNA.

43. A method as claimed in claim 42 in which the primer extension product of one allele specific primer can act as the template for an allele specific primer for a different polymorphic locus in a polymerase chain reaction.

44. A type specific primer for amplifying internal repeat units of one type within a telomere repeat array consisting essentially of at least one sequence selected from the group consisting of:

Te1H (SEQ ID NO:12)
   5'-CCCTAACCCTAACCCTAACCCTA-3',
Te1G (SEQ ID NO:13)
   5'-CCCTCACCCTCACCCTCACCCTC-3',
Te1W (SEQ ID NO:14)
   5'-CCCTTACCCTTACCCTNACCCTA-3',
Te1X (SEQ ID NO:15)
   5'-CCCTTACCCTTACCCTNACCCTC-5',
Te1Y (SEQ ID NO:16)
   5'-CCCTTACCCTTACCCTNACCCTG-3',
TAG-Te1W (SEQ ID NO:18)
   5'-TCATGCTCCATGGTCCGGACCCTTACCCTTAC
   CCTNACCCTA-3',
TAG-Te1X (SEQ ID NO:19)
   5'-TCATGCGTCCATGGTCCGGACCCTTACCCTA
   CCCTNACCCTC-3', and
TAG-Te1Y (SEQ ID NO:20)
   5'-TGATGCGTCCATGGTCCGGACCCTTACCCTTA
   CCCTNACCCTG-3'.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 1:

GAGTGAAAGA ACGAAGCTTC C                                              21

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 2:

CCCTCTGAAA GTGGACCTAT                                                20

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 3:

GCGGTACCAG GGACCGGGAC AAATAGAC                                       28

(2) INFORMATION FOR SEQ ID NO: 4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 4:

GCGGTACCTA GGGGTTGTCT CAGGGTCC                                       28

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 5:

CGGAATTCCA GACACACTAG GACCCTGA                                       28

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single (D) TOPOLOGY: linear (xi) SEQUENCE DESCRIPTION: SEQ ID NO: 6:

GAATTCCTGG GGACTGCGGA TG                                                    22

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 7:

CATCCCTGAA GAAGCATCTT GGCC                                                  24

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 8:

AGACGGGGAC TCCCGAGC                                                         18

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 9:

CTGCTTTTAT TCTCTAATCT GCTCCCA                                               27

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 10:

CTTTTATTCT CTAATCTGCT CCCT                                                  24

(2) INFORMATION FOR SEQ ID NO: 11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 11:

ACCCTCTGAA AGTGGACCA                                                        19

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 12:

CCCTAACCCT AACCCTAACC CTA                              23

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 13:

CCCTCACCCT CACCCTCACC CTC                              23

(2) INFORMATION FOR SEQ ID NO: 14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 14:

CCCTTACCCT TACCCTNACC CTA                              23

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 15:

CCCTTACCCT TACCCTNACC CTC                              23

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 16:

CCCTTACCCT TACCCTNACC CTG                              23

(2) INFORMATION FOR SEQ ID NO: 17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 17:

CTGCTTTTAT TCTCTAATCT GCTCCCT                          27

(2) INFORMATION FOR SEQ ID NO: 18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 18:

TCATGCGTCC ATGGTCCGGA CCCTTACCCT TACCCTNACC CTA                  43

(2) INFORMATION FOR SEQ ID NO: 19:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 19:

TCATGCGTCC ATGGTCCGGA CCCTTACCCT TACCCTNACC CTC                  43

(2) INFORMATION FOR SEQ ID NO: 20:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 20:

TGATGCGTCC ATGGTCCGGA CCCTTACCCT TACCCTNACC CTG                  43

(2) INFORMATION FOR SEQ ID NO: 21:

(i) SEQUENCE CHARACTERISTICS:
        (A) LENGTH: 882 base pairs
        (B) TYPE: nucleic acid
        (C) STRANDEDNESS: single
        (D) TOPOLOGY: linear (xi) SEQUENCE DESCRIPTION: SEQ ID NO: 21:

```
CAGGGACCGG GACAAATAGA CGGGGACTCC CGAGATGAGA AAGACCTTTT CGTACAAAGT     60

GTTTGCATCA GTACCTCACA ATGAAAAGAA TAAGATAAAT AACAGTACAA AAAAGCAATC    120

ACCAGATCAG CTCAAGGCAC TCTTTGAAGT CCCCCCTGTG TAGGGAAGTT GGAAGACATA    180

TCTGTGTGGC CCATAGAGAG TAGATCCCAA AGACAGAAGG CCCAAGTCCC TAAATCCCAC    240

AGGGGAACTG TGTTACAGAC CAGGAGCTCA TGTACAGGGC TGTCCCAGGG CCCCTAAATT    300

CCAGAAGGGA ACTGGGTTAG AGTCCAGGGG CTCATGCAAC GGGCTGTCCC TGGTCCCCTA    360

AATCCCCACA GGGGAACTGG GTTAGAGATG AGGAGCTCAT TTTCCGGGCT GTCCAGGTCC    420

CCTAAATCCC AGATGGGAAC TGGGTTATCA ACCAGGTGCT CTTCTAGGGG TTGTCTCAGG    480

GTCCTAGTGT GTCTGGAATT GGTGGGTTCT TGGTCTCACT GACTTCAAGA ATGAAGACGC    540

GGAACCTCGC GGTGAGTGTT ACAGTTCTTA AAGGTGGCGC GTCCGGAGTT TGTTTCTTCT    600

GATGTTCAGA TGTGTTCTGA GTTTCTTCTT TCTGGTGGGG TTGTGGTCTC ACTGGCTCAG    660

GAGTGAAGCT GCAGACCTTT GCGGTGAGTG TCACAGCTCA TAAAGGCAGT GTGGACCCAA    720

AGAGTGAGCA ATAGCAAGAT TTATTGCAAA GAGTGAAAGA ACGAAGCTTC CACAGTATGG    780

AAAGGGACCC CATTGGGTTG CCACTGCTGG CTCAGGCAGT CTGCTTTTAT TCTCTAATCT    840

GCTCCCACCC ACATCCTGCT GATAGGTCCA CTTTCAGAGG GT                      882
```

(2) INFORMATION FOR SEQ ID NO: 22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear -continued (xi) SEQUENCE DESCRIPTION: SEQ ID NO: 22:

CTGCTTTTAT TCTCTAATCT GCTCCCT                                                                                          27